United States Patent
Arndt et al.

(10) Patent No.: US 6,713,661 B1
(45) Date of Patent: Mar. 30, 2004

(54) ABSORBENT ARTICLES PROVIDING IMPROVED FIT WHEN WET

(75) Inventors: Silke Arndt, Darmstadt (DE); Bruno Johannes Ehrnsperger, Frankfurt (DE); Mattias Schmidt, Idstein (DE); Gary Dean Lavon, Oberursel (DE); Carsten Heinrich Kruezer, Sulzbach (DE); Claus Peter Stoelzel, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/674,057

(22) PCT Filed: Apr. 23, 1999

(86) PCT No.: PCT/IB99/00741

§ 371 (c)(1),
(2), (4) Date: Oct. 25, 2000

(87) PCT Pub. No.: WO99/55264

PCT Pub. Date: Nov. 4, 1999

(30) Foreign Application Priority Data

Apr. 28, 1998 (US) ................................. PCT/US98/08515

(51) Int. Cl.[7] ................................................ A61F 13/15
(52) U.S. Cl. ............................... 604/378; 604/385.101; 604/367; 604/366
(58) Field of Search ................................. 604/359, 366, 604/368, 369, 374, 375, 378, 385.3, 385.23

(56) References Cited

U.S. PATENT DOCUMENTS

| | | |
|---|---|---|
| 3,224,926 A | 12/1965 | Bernardin |
| RE26,152 E | 1/1967 | Andren ............................ 29/33 |
| 3,301,746 A | 1/1967 | Sanford et al. |
| 3,440,135 A | 4/1969 | Chung |
| 3,556,932 A | 1/1971 | Coscia et al. |
| 3,661,875 A | 5/1972 | Sieja |
| 3,699,103 A | 10/1972 | Kiss |
| 3,770,731 A | 11/1973 | Jaeger |
| 3,860,003 A | 1/1975 | Buell .......................... 128/287 |
| 3,932,209 A | 1/1976 | Chatterjee |
| 4,035,147 A | 7/1977 | Sangenis et al. |
| 4,062,817 A | 12/1977 | Westerman |
| 4,076,663 A | 2/1978 | Masuda et al. |
| 4,193,776 A | 3/1980 | Wasala et al. |
| 4,340,706 A | 7/1982 | Obayashi et al. |
| 4,483,743 A | 11/1984 | Turbak et al. |
| 4,506,052 A | 3/1985 | Furukawa et al. |
| 4,541,871 A | 9/1985 | Obayashi et al. |
| 4,587,308 A | 5/1986 | Makita et al. |
| 4,590,114 A | 5/1986 | Holtman |
| 4,610,678 A | 9/1986 | Weisman et al. |
| 4,625,001 A | 11/1986 | Tsubakimoto et al. |
| 4,666,983 A | 5/1987 | Tsubakimoto et al. |
| 4,673,402 A | 6/1987 | Weisman et al. |
| 4,734,478 A | 3/1988 | Tsubakimoto et al. |
| RE32,649 E | 4/1988 | Brandt et al. |
| 4,735,987 A | 4/1988 | Morita et al. |

(List continued on next page.)

FOREIGN PATENT DOCUMENTS

| | | |
|---|---|---|
| EP | 0 509 708 B1 | 10/1992 |
| EP | 0 640 330 B1 | 3/1995 |
| EP | 0 774 242 B1 | 5/1997 |

(List continued on next page.)

*Primary Examiner*—Weilun Lo
*Assistant Examiner*—Jacqueline Stephens
(74) *Attorney, Agent, or Firm*—Matthew P. Fitzpatrick; Ken K. Patel; Steven W. Miller

(57) ABSTRACT

An absorbent article having improved fit and comfort. The absorbent core is designed such that fluid is moved substantially from the crotch region to the waist regions. Preferred absorbent covers have an acquisition region, a distribution region, and a storage region.

17 Claims, 6 Drawing Sheets

U.S. PATENT DOCUMENTS

| | | |
|---|---|---|
| 4,737,582 A | 4/1988 | Goldman et al. |
| 4,773,903 A | 9/1988 | Weisman et al. |
| 4,789,861 A | 12/1988 | Baggett et al. |
| 4,822,453 A | 4/1989 | Dean et al. |
| 4,824,901 A | 4/1989 | Alexander et al. |
| 4,888,093 A | 12/1989 | Dean et al. |
| 4,888,231 A | 12/1989 | Angstadt |
| 4,898,642 A | 2/1990 | Moore et al. |
| 4,935,022 A | 6/1990 | Lash et al. |
| 4,976,819 A | 12/1990 | Minton |
| 4,994,037 A | 2/1991 | Bernardin et al. .......... 604/368 |
| 5,061,259 A | 10/1991 | Goldman et al. |
| 5,098,423 A | 3/1992 | Pieniak et al. ........... 604/385.1 |
| 5,102,597 A | 4/1992 | Roe et al. |
| 5,164,459 A | 11/1992 | Kimura et al. |
| 5,167,897 A | 12/1992 | Weber et al. |
| 5,180,622 A | 1/1993 | Berg et al. |
| 5,190,563 A | 3/1993 | Herron et al. |
| 5,217,445 A | 6/1993 | Young et al. |
| 5,244,541 A | 9/1993 | Minton |
| 5,260,345 A | 11/1993 | DesMarais et al. |
| 5,290,820 A | 3/1994 | Brownscombe et al. |
| 5,352,711 A | 10/1994 | DesMarais |
| 5,387,207 A | 2/1995 | Dyer et al. |
| 5,409,771 A | 4/1995 | Dahmen et al. |
| 5,468,536 A | 11/1995 | Whitcomb et al. |
| 5,486,410 A | 1/1996 | Groeger et al. |
| 5,558,655 A | 9/1996 | Jezzi et al. ................. 604/378 |
| 5,560,222 A | 10/1996 | Perron |
| 5,560,878 A | 10/1996 | Dragoo et al. |
| 5,562,646 A | 10/1996 | Goldman et al. |
| 5,563,179 A | 10/1996 | Stone et al. |
| 5,583,162 A | 12/1996 | Li et al. |
| 5,599,335 A | 2/1997 | Goldman et al. |
| 5,643,588 A | 7/1997 | Roe et al. ................... 424/402 |
| 5,650,222 A | 7/1997 | DesMarais et al. |
| 5,653,922 A | 8/1997 | Li et al. |
| 5,786,395 A | 7/1998 | Stone et al. |
| 5,827,909 A | 10/1998 | DesMarais |
| 5,851,648 A | 12/1998 | Stone et al. |
| 6,013,589 A | 1/2000 | DesMarais et al. |
| 6,083,211 A | 7/2000 | DesMarais |
| 6,107,356 A | 8/2000 | DesMarais |
| 6,107,538 A | 8/2000 | Young et al. |
| 6,121,509 A | 9/2000 | Ashraf et al. |
| 6,372,953 B1 | 4/2002 | Young et al. |
| 6,426,445 B1 | 7/2002 | Young et al. |
| 6,551,295 B1 | 4/2003 | Schmidt et al. |

FOREIGN PATENT DOCUMENTS

| | | | |
|---|---|---|---|
| EP | 0 797 966 A1 | 10/1997 | |
| EP | 0 797 968 | 10/1997 | ........... A61F/13/15 |
| EP | 0 799 966 A2 | 10/1997 | |
| EP | 0 810 078 A1 | 12/1997 | |
| EP | 0 820 746 | 1/1998 | ........... A61F/13/15 |
| WO | WO 90/08789 A1 | 8/1990 | |
| WO | WO 92/16565 A1 | 10/1992 | |
| WO | WO 93/05080 A1 | 3/1993 | |
| WO | WO 93/16669 A1 | 9/1993 | |
| WO | WO 98/22067 | 5/1998 | ........... A61F/13/15 |
| WO | WO 98/43571 | 10/1998 | ........... A61F/13/15 |
| WO | WO 98/43578 A1 | 10/1998 | |
| WO | WO 98/43580 | 10/1998 | ........... A61F/13/15 |

ABSORBENT ARTICLES PROVIDING IMPROVED FIT WHEN WET

FIELD OF THE INVENTION

The present invention relates to absorbent structures useful in absorbent articles such as diapers, incontinent briefs, training pants, diaper holders and liners, sanitary hygiene garments, and the like. More particularly, the invention relates to absorbent structures that provide articles having improved fit and comfort when dry and particularly when wetted with bodily fluids.

BACKGROUND OF THE INVENTION

Infants and other incontinent individuals wear absorbent articles such as diapers to absorb and retain urine and other body exudates. Absorbent articles function both to contain the discharged materials and to isolate these materials from the body of the wearer and from the wearer's garments and bed clothing. Disposable absorbent articles having many different basic designs are known in the art. For example, U.S. Pat. No. Re. 26,152, entitled "Disposable Diaper" issued to Duncan and Baker on Jan. 31, 1967, describes a disposable diaper which has achieved wide acceptance and commercial success. U.S. Pat. No. 3,860,003, entitled "Contractable Side Portions For Disposable Diaper", issued to Buell on Jan. 14, 1975, describes an elastic leg cuff disposable diaper which has achieved wide acceptance and commercial success.

Many diaper designs are relatively wide and bulky, when dry and particularly when wet, in the region of the article that fits between the legs of the wearer. This results in a certain level of discomfort to the wearer, as these diapers tend to bunch when worn. In an effort to address wearer discomfort, U.S. Pat. No. 4,610,678 (Weisman et al.) describes diapers comprising densified cores that are thinner in this region than were prior designs. Nonetheless, even these articles store significant levels of absorbed fluids in the discharge region of the article. This discharge region is positioned within the portion of the article that fits in the wearer's crotch region when worn.

Since prior absorbent articles do not effectively distribute fluid, these articles are typically designed to store significant quantities of fluid in the crotch region of the diaper. Thus, upon each loading, this region of the article becomes increasingly bulky and therefore tends to be more uncomfortable for the wearer. See, for example, U.S. Pat. No. 5,098,423 to Pieniak et al., which builds on the disclosure of the Weisman patent, and describes a low dry bulk disposable diaper. The focus of the '423 patent is an article having a relatively low cross sectional area, when dry, particularly in the "impact zone" (defined in the patent as the second and third fifths of the article's length). Indeed, an important aspect of the described articles is the ability of the absorbent material in the impact zone to absorb fluid. The patent specifically indicates that at least 60% of the total absorbed fluid is retained in the diaper's impact zone. Thus, while the patent discusses the desire for improved fit when dry, it fails to address the issue of providing improved fit and comfort throughout the entire wearing period. Moreover, the primary consideration for improving fit is on thin and wide structures which fold and bunch during use, without optimizing narrowness and bulk, dry and wet, of the absorbent material in the crotch region. Accordingly, the articles described in the '423 patent have in the crotch region an overall low cross sectional area when dry, accomplished by providing a relatively thin (i.e., in the article's the z-dimension), relatively wide (i.e., in the article's x-dimension) core. However, the core retains 60% of its absorbent capacity in the crotch region. This results in excess bulk, thickness, thereby reducing the comfort and fit when the article is wetted with body fluid.

Several attempts have been made to provide articles, such as diapers, with increased storage capacity outside of the crotch region. U.S. Pat. No. 4,994,037 (Bernardin, et al.) discloses diapers with absorbent core designs comprising superabsorbent material located in either one or both waist regions of the absorbent core. The structures described therein show low efficiencies of the material usage in the waist regions of the article, because of substantially higher capacity in the crotch region than in either of the waist regions. Although it is pointed out in U.S. Pat. No. 4,994,037, that the superabsorbent material does absorb some liquid, it is not recognized therein that the liquid pick up further away form of the loading area is still significantly reduced. In addition, the reference describes the use of fluff components, especially around the loading region, which thus inevitably will result in a high rewetting tendency of the article.

It therefore would be advantageous to provide an absorbent structure that provides better fit and wearer comfort, even after the structure is wetted with body fluids. It would be further advantageous to provide an absorbent structure which has reduced bulk in the crotch region in both the dry and wet states. Such structures would provide absorbent articles having improved fit and comfort, even when wetted with body fluids.

Therefore, it is an object of the present invention to provide an absorbent structure having improved fit on the wearer during use by reducing the structure's crotch width dry as well as when the structure is wetted with fluid.

It is a further object of the present invention to provide an absorbent structure that provides reduced caliper in the crotch region of the product when dry as well as when wet which in turn positively impacts comfort and fit.

It is a further object of the present invention to provide an absorbent structure that provides improved comfort for the wearer resulting from the structure's ability to readily acquire, distribute and store a significant amount of fluid remote from the crotch region of the structure.

It is a further object of the present invention to provide absorbent articles which have low rewet values, thereby providing improved skin dryness.

It is a further object of the present invention to provide articles that more effectively distribute body exudates such that higher absorbent capacities can be achieved even against gravitational forces.

It is a further object of the invention to provide absorbent articles comprising these absorbent structures.

These and other objects of the present invention will be more readily apparent when considered in reference to the following description and when taken in conjunction with the accompanying drawings.

SUMMARY OF THE INVENTION

The present invention provides absorbent structures for inclusion in absorbent articles such as diapers, incontinent briefs, training pants, diaper holders and liners, feminine hygiene garments, and the like, designed to provide improved fit and comfort for the wearer while adequately containing body exudates. Such an absorbent article has a containment assembly (chassis) typically comprising a liquid pervious topsheet and a substantially liquid impervious backsheet, and an absorbent core associated with the outer covering layer. The absorbent core is designed so as to be relatively narrow and thin in the crotch region of the diaper, even when the core absorbs significant amounts of fluid during use. To achieve this, the absorbent core is designed such that fluid is moved substantially from the crotch region to the front and/or rear waist regions of the article.

Thus, the absorbent article has an absorbent capacity as determined by the Whole Article Vertical Wicking test, wherein capacities are determined for segments of the article positioned in vertical distance away from the folding line of the article, and wherein the absorbent capacity for a segment at 13.5 cm is at least 0.5 times the capacity for the segment at 0 cm, preferably at least 0.75 times, more preferably 1.25, and most preferably at least two times.

Suitable absorbent articles can also be described by respective calipers at the crotch, namely by the Saturated Crotch Caliper (SCC), and the Actual Wet Crotch Caliper (AWCC), which are determined following the Curved Acquisition test method, whereby the Actual Wet Crotch Caliper is less than the Saturated Crotch Caliper, whilst the article provides a good rewet performance by exhibiting a Post Curved Acquisition Rewet Value of less than about 180 mg.

A suitable absorbent article can also be described by comprising an absorbent core, which has a crotch region and one or more waist regions, whereby the article and the core have a characteristic crotch point and characteristic waist points positioned just outside of the crotch regions, whereby the Actual Wet Crotch Caliper as determined following the Curved Acquisition test method at the crotch point, is less than the Actual Wet Waist Caliper, as determined following the Curved Acquisition test method at a waist point, and the article provides for a good rewet performance by exhibiting a Post Curved Acquisition Rewet Value of less than about 180 mg.

A preferred embodiment of the article according to the present invention comprises an absorbent core with a crotch region and one or more waist regions, which core comprises an acquisition region, a distribution region, a storage region, and a storage/rewet barrier means, which is positioned on the surface of said storage region, which is oriented towards the wearer during use, and which comprises absorbent gelling material.

Preferably, the absorbent article has an Actual Wet Crotch Caliper (AWCC) of less than about 20 mm, preferably less than 15 mm, more preferably less than 10 mm, most preferably less than 5 mm. The absorbent article can have an AWCC of less than 90% of the article's SCC, preferably less than 50%, more preferably less than 25%. The crotch width of absorbent articles according to the present invention is preferably less than about 90 mm, preferably less than 70 mm, more preferably less than 50 mm. Preferably, the article according to the present invention Dry Crotch Caliper of less than 8 mm preferably less than 5 mm, more preferably less than 3 mm.

When submitting the articles according to the present invention the Curved Acquisition test, they exhibit an initial acquisition rate of at least 5 ml/usec, preferably of at least 10 ml/sec, more preferably greater than 15 ml/sec, or a $4^{th}$ gush acquisition rate of at least 0.25 mi/sec, preferably at least 0.50 ml/sec, more preferably at least 1.0 ml/sec.

When submitting articles according to the present invention the Post Curved Acquisition Collagen Rewet test, they preferably exhibit a value of less than 150 mg, more preferably less than 100 mg, even more preferably less than 50 mg. For articles comprising a rewet barrier, the Post Curved Acquisition Collagen Rewet is preferably less than the Post Curved Acquisition Collagen Rewet of the absorbent article wherein said rewet barrier region is removed. Preferred materials for the rewet barrier are superabsorbent gelling materials, hydrogels, or superabsorbents; polymeric foam material; HIPE based foams, or combinations thereof.

Absorbent articles according to the present invention can comprise an acquisition region which preferably comprises a material, which has a Medium Desorption Pressure (MDP) value corresponding to a height of less than 15 cm, preferably less than 12 cm, more preferably less than 10 cm, but preferably of more than 5 cm.

In a preferred embodiment, the absorbent core of an absorbent article comprises a liquid acquisition region, a liquid distribution region, and a liquid storage region, whereby at least a portion of the storage region is positioned between the distribution region and the wearer oriented surface of the article during use. The storage region can comprise two separated subregions positioned longitudinally offset from each other. Preferably, the crotch region of the absorbent article has an ultimate storage capacity of less than about 40% of the total ultimate storage capacity of the absorbent core, preferably less than 25%, more preferably less than 10%.

A further preferred article according to the present invention comprises a moisture vapor permeable backsheet. Such an article can comprise an absorbent core which covers a surface area that is less than 60% of the surface area of the moisture vapor permeable backsheet in the crotch region, preferably less than 50%, more preferably less than 25%. The moisture vapor permeable backsheet can comprise microporous films or laminates, nonwovens, monolithic films or combinations thereof, such as laminates.

Absorbent article according to the present invention can comprise distribution material having a liquid flux at 12.4 cm of more than 0.075 g/cm$^2$/sec, preferably more than 0.1 g/cm$^2$/sec, more preferably more than 0.15 g/cm$^2$/sec), when measured according to the Distribution Material Vertical Wicking test, or which have a time to wick to 12.4 cm of less than 300 sec. preferably less than 100 sec, more preferably more than 50 sec when measured according to this test.

Absorbent articles according to the present invention comprise a liquid distribution material having a Capillary sorption desorption height at 90% of desorbed capacity of at least 40 cm. Such materials can be fibrous or foamed liquid distribution materials.

Absorbent articles according to the present invention can comprise an ultimate storage material in the absorbent core, which satisfies at least one of the following requirements of (a) a Capillary Sorption Absorption Capacity at 35 cm (CSAC 35) of at least 15 g/g; and/or (b) a Capillary Sorption Absorption Capacity at 0 cm (CSAC 0) of at least 15 g/g and a Capillary Sorption Absorption Efficiency at 40 cm (CSAE 40) of at least 55%; and/or (c) a Capillary Sorption Absorption Height at 50% of its capacity at 0 cm absorption height (CSAH 50) of at least 35 cm.

A preferable ultimate storage material can comprise a polymeric foam material, preferably derived from high internal phase water-in-oil emulsions, a high surface area fibers, a hydrogel forming materials, or combinations thereof.

Articles according to the present invention preferably further comprise a feces management means positioned between the topsheet of the article, which is oriented towards the wearer during its intended use and the backsheet positioned opposed to the topsheet, providing for a trans-topsheet capacity of at least 0.2 grams per square inch. Preferably, the feces management means is a fibrous web, or a web comprising a backing and a sheet of fibers, which has anchor portions in the backing at spaced bonding locations and has arcuate portions of the sheet projecting from said backing between bonding locations, or an apertured formed film.

The topsheet of the article can be an apertured structure, having a liquid pervious structured carrier with an inner surface oriented towards the interior of the article and an outer surface oriented toward the skin of the wearer when the article is worn, whereby the structured carrier has an effective open area of at least about 12 percent and a plurality of apertures with an effective size greater than 0.1 square millimeters. Optionally, the outer surface of the structured carrier comprises an effective amount of a skin care composition which is semi-solid or solid at 20° C. and which is partially transferable to the wearer's skin.

BRIEF DESCRIPTION OF THE DRAWINGS

While the specification concludes with claims particularly pointing out and distinctly claiming the subject matter which is regarded as forming the present invention, it is believed that the invention will be understood from the following description which is taken in conjunction with the accompanying drawings in which like designations are used to designate substantially identical elements, and in which:

DETAILED DESCRIPTION OF THE INVENTION

Figure 1:
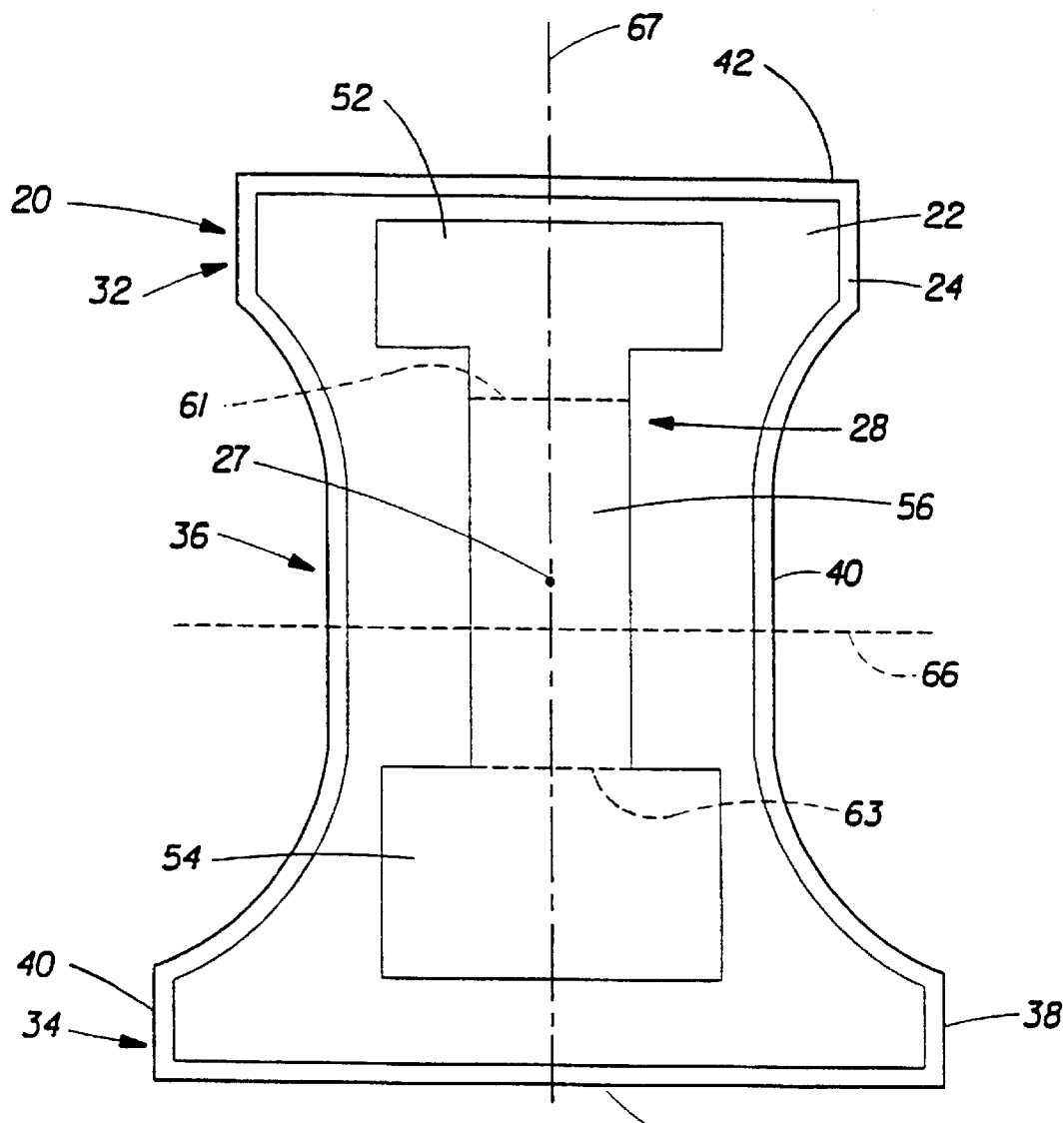
FIG. 1 is a top plan view of an absorbent article according to the present invention where the topsheet is transparent so as to more clearly show the absorbent core.

As used herein, the term "absorbent article" refers to devices which absorb and contain body exudates, and, more specifically, refers to devices which are placed against or in proximity to the body of the wearer to absorb and contain the various exudates discharged from the body. Absorbent articles include devices designed to absorb urine, which are used by incontinent persons. Such incontinent articles include but are not limited to diapers, adult incontinent briefs, training pants, diaper holders and liners. Other absorbent articles include those designed to absorb blood-based fluids such as menses. Such sanitary hygiene articles include tampons, catamenial pads, and the like. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

As used herein, the term "absorbent core" refers to the portions (e.g., layers) of an absorbent article whose function are to acquire, distribute, transfer, store and/or redistribute fluid. Acquisition materials include materials whose primary function is to acquire then relinquish fluids. Such materials include acquisition layers, topsheet materials, transfer layers, flow control modules, wrap tissues or nonwoven sheets designed to prevent migration of hydrogel forming polymers, etc. As used herein, the term "distribution material" refers to the absorbent core material(s) whose primary function is to absorb and distribute/redistribute fluid to points away from the point of initial fluid loading. As used herein, the term "storage material" refers to the absorbent core material that retains the majority of the fluid absorbed by the article. It should be understood that the terms "distribution material" and "storage material" are not mutually exclusive. In certain embodiments, a single material may function to provide both fluid distribution and fluid storage.

As used herein, the term "front" refers to the portion of an article or absorbent core that is intended to be positioned proximate the front of a wearer. The term "rear" refers to the portion of an article or absorbent core that is intended to be positioned proximate the back of the wearer. As such, use of the relative term "in front of" means a position in the article or core more toward the front of the article or core, while the term "behind" means a position in the article or core more toward the rear of the article or core.

As used herein, the term "z-dimension" refers to the dimension orthogonal to the length and width of the member, core or article. The z-dimension corresponds generally to the thickness of the member, core or article.

As used herein, the term "x-y dimension" refers to the plane orthogonal to the thickness of the member, core or article. The x- and y-dimensions correspond generally to the width and length, respectively, of the member, core or article.

The "crotch point" of an article and the article's absorbent core is determined by placing the article on a wearer then placing the wearer in a standing position and then placing an extensible filament around the legs in a figure eight configuration. (See FIG. 4.) The point in the article and the absorbent core corresponding to the point of intersection of the filament is deemed to be the crotch point of the article and the absorbent core. It is understood that the crotch point is determined by placing the absorbent article on a wearer in the intended manner and determining where the crossed filament would contact the article and the absorbent core.

As referred to herein, the "crotch region" of an absorbent core corresponds to 50% of the absorbent core's total length (i.e., in the y-dimension), where the crotch point is located in the longitudinal center of the crotch region. That is, the crotch region is determined by first locating the crotch point of the absorbent core, and then measuring forward and backward a distance of 25% of the core's total length.

As used herein, the term "crotch width" refers to the width in the crotch region of the absorbent core that is the narrowest when measured at the crotch point. When this layer consists of a plurality of discrete layers, the layer having the smallest width is the width of that layer, and therefore is the crotch width of the absorbent core. If a layer is profiled in the cross (x-) dimension, the width of the layer is determined by the width of the highest basis weight region of the profile.

As used herein, the term "layers" refers to identifiable components of the absorbent structure, and any structure referred to as a "layer" may actually comprise a laminate or combination of several sheets or webs of the requisite type of materials as hereinafter described. As used herein, the term "layer" includes the terms "layers" and "layered." For purposes of this invention, it should also be understood that the term "upper" refers to the layer of the absorbent core which is nearest to and faces the article topsheet; conversely, the term "lower" refers to the layer of the absorbent core which is nearest to and faces the article backsheet. It should be noted that the various members, layers, and structures of absorbent articles according to the present invention may or may not be generally planar in nature, and may be shaped or profiled in any desired configuration.

An embodiment of the an absorbent article in the form of a diaper 20 having one such absorbent core according to the present invention is shown in FIG. 1. FIG. 1 is a top plan view of diaper 20 in a flat-out, uncontracted state (i.e., with any elastic-induced contraction removed) having a topsheet 22, a backsheet 24, and an absorbent core indicated generally as 28 that is positioned between topsheet 22 and backsheet 24. Topsheet 22 is shown as being transparent so as to better illustrate the absorbent core 28.

As is also shown in FIG. 1, diaper 20 has a front waistband region 32, a back waistband region 34, a center region 36 and a periphery 38 that is defined by the outer edge of backsheet 24 and which has longitudinal edges designated 40 and end edges designated as 42. The longitudinal axis of diaper 20 runs essentially parallel to longitudinal edges 40 and is depicted as longitudinal centerline 67 (and corresponds to the y-direction or length), while the transverse axis runs essentially parallel to end edges 42 and is depicted as transverse centerline 66 (and corresponds to the x-direction or width). The waistband regions 32 and 34 comprise those upper portions of the diaper 20, which when worn, encircle the waist of the wearer. The center region 36 is that portion of the diaper 20 between waistband regions 32 and 34, and comprises that portion of the diaper 20 which when worn, is positioned between the legs of the wearer and covers the lower torso of the wearer. Thus, the center region 36 defines the area of typical liquid deposition for a diaper 20 or other disposable absorbent article.

Topsheet 22 and backsheet 24 can be associated together in any suitable manner. As used herein, the term "associated" encompasses configurations where topsheet 22 is directly joined to backsheet 24 by affixing the topsheet directly to the backsheet, and configurations where the topsheet is indirectly joined to the backsheet by affixing the topsheet to intermediate members which in turn are affixed to the backsheet. Preferably, the topsheet 22 and backsheet 24 are affixed directly to each other by attachment means (not shown) such as an adhesive or any other attachment means as known in the art. For example, a uniform continuous layer of adhesive, a patterned layer of adhesive, or an array of separate lines or spots of adhesive may be used to affix topsheet 22 to backsheet 24. As shown in FIG. 1, topsheet 22 has a slightly smaller size configuration than backsheet 24. However, topsheet 22 and backsheet 24 can both have the same size configuration (i.e., are coextensive) such they are joined together at periphery 38 of diaper 20. The size of the backsheet 24 is dictated in part by the size of the absorbent core 28 and the exact diaper design selected. In the embodiment shown in FIG. 1, the backsheet 24 has an hourglass-shaped configuration. However, other configuration such as rectangular, I-shaped and the like are also suitable.

Although not shown, diaper 20 can have elastic members that exert a contracting force on the diaper so that it configures more closely and more comfortably to the wearer. These elastic members can be assembled in a variety of well known configurations, such as those described generally in U.S. Pat. No. 3,860,003 (Buell), issued Jan. 14, 1975, which patent is incorporated by reference. The elastic members can be disposed adjacent the periphery 38 of the diaper 20, preferably along each longitudinal edge 40, so that the elastic members tend to draw and hold the diaper 20 against the legs of the wearer. Alternatively, the elastic members can be disposed adjacent either or both of the end edges 42 of diaper 20 to provide a waistband as well as or rather than leg cuffs. See, for example, U.S. Pat. No. 4,515,595 (Kievit et al.), issued May 7, 1985, which is incorporated by reference. The elastic members are secured to the diaper 20 in an elastically contractible condition so that in a normally unrestrained configuration, these elastic members effectively contract or gather the diaper 20. The elastic members can be secured in an elastically contractible condition in at least two ways. For example, the elastic members can be stretched and secured while the diaper 20 is in an uncontracted condition. Alternatively, the diaper 20 can be contracted, for example, by pleating, and the elastic members secured and connected to the diaper 20 while they are in their unrelaxed or unstretched condition. The elastic members can extend essentially the entire length of the diaper 20 in the center region 36, or alternatively can extend the entire length of the diaper 20, or any other length suitable to provide an elastically contractible line. The length of these elastic members is typically dictated by the diaper's design.

Referring to FIG. 1, absorbent core 28 is depicted in an "I" configuration. As is indicated above, the absorbent core will comprise front and rear regions, as well as a crotch region. These regions are defined by determining the crotch point of core 28 in accordance with the description herein. As discussed above, the crotch point is determined by reference to the wearer's anatomy. For purposes of illustration only, the crotch point of core 28 is depicted as item 27 in FIG. 1. Crotch point 27 is depicted as being located on the longitudinal centerline 67 of diaper 20 and absorbent core 28. This will generally be the case, regardless of the configuration of the diaper and absorbent core. However, as indicated, crotch point 27 is not located on transverse centerline 66 in this particular embodiment, though it may be in other diaper/core designs. As is discussed above, once the crotch point of absorbent core 28 is determined, the crotch region is determined by measuring forward from the crotch point a distance of 25% of the core's total length (depicted as transverse line 61) and backward from the crotch point a distance of 25% of the core's total length (depicted as transverse line 63). In this illustration, the crotch region is the region of the core located between transverse lines 61 and 63. As depicted in FIG. 1, absorbent core 28 is shown to have a front region 52, a back region 54, and a crotch region 56. Again, the crotch region 56 of core 28 is dictated by the location of the crotch point in the core. The crotch region of the core can be used to define the corresponding crotch region of the article.

The topsheet 22 is preferably compliant, soft feeling, and non-irritating to the wearer's skin. Further, the topsheet is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet can be made of a hydrophobic material to isolate the wearer's skin from liquids contained in the absorbent core that is treated on at least one side with a surfactant to allow liquids to readily penetrate through its thickness.

At least a portion of the topsheet can be subjected to mechanical stretching in order to provide a "zero strain" stretch laminate that forms the elastic side panels. To achieve this, the topsheet is preferably elongatable, most preferably drawable, but not necessarily elastomeric, so that the topsheet will, upon mechanical stretching, be at least to a degree permanently elongated such that it will not fully return to its original configuration. The topsheet can be subjected to mechanical stretching without undue rupturing or tearing of the topsheet, for which it is preferred that the topsheet have a low cross-machine direction (lateral direction) yield strength.

There are a number of manufacturing techniques which may be used to manufacture the topsheet. For example, the topsheet may be a nonwoven web of fibers. When the topsheet comprises a nonwoven web, the web may be spunbonded, carded, wet laid, meltblown, hydroentangled, combinations of the above, or the like. A preferred topsheet is carded and thermally bonded by means well known to those skilled in the fabrics art. A preferred topsheet comprises staple length polypropylene fibers having a denier of about 2.2. As used herein, the term "staple length fibers" refers to those fibers having a length of at least about 15.9 mm (0.625 in). Preferably, the topsheet has a basis weight from about 18 to about 25 g/m². A suitable topsheet is manufactured by Veratec, Inc., a division of International Paper Company, of Walpole, Mass., under the designation P-8.

The topsheet 22 is positioned above the body surface of the absorbent core 28. In preferred embodiments, an acquisition material is positioned between absorbent core 28 and topsheet 22. Topsheet 22 can be joined to the absorbent core 28 and/or backsheet 24 by attachment means (not shown) such as those well known in the art. Suitable attachment means are described below with respect to joining the topsheet 22 and/or backsheet 24 to the absorbent core 28. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet and the backsheet are joined directly to each other in the diaper periphery and can be indirectly joined together by directly joining them to the absorbent core by the attachment means (not shown). In an alternative embodiment, the absorbent core (or the preferred acquisition material) need not be joined to either the topsheet or the backsheet such that the absorbent core is allowed to "float" between them.

The topsheet can comprise a structured carrier material as disclosed in Roe et al. P&G case CM1640, PCT Application No. PCT/US97120842. The structured carrier is compliant, soft feeling, and non-irritating to the wearer's skin. Further, the structured carrier is liquid pervious, permitting liquids (e.g., urine) to readily penetrate through its thickness. A suitable structured carrier may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the structured carrier is made of a hydrophobic material to isolate the wearer's skin from liquids contained in the absorbent core. Alternatively, the structured carrier may be surfactant treated to make it hydrophilic.

The structured carrier preferably has a plurality of apertures with an effective aperture size of at least 0.2 square millimeters, more preferably, the plurality of apertures have an effective aperture size of at least 0.5 square millimeters, even more preferably, the plurality of apertures have an effective aperture size of at least 1.0 square millimeters, and most preferably, the plurality of apertures have an effective aperture size of at least 2.0 square millimeters. Effective apertures are those which have a gray level of 18 or less on a standard gray level scale of 0-255, under the image acquisition parameters described in Roe et al. P&G case CM1640, PCT Application No. PCT/US97/20842.

The structured carrier preferably has an effective open area of at least 15 percent, more preferably the structured carrier has an effective open area of at least 20 percent, even more preferably, the structured carrier has an effective open area of at least 25 percent, and most preferably the structured carrier has an effective open area of at least 30 percent. Carriers thusly constructed are particularly effective in receiving fecal matter, and provide a trans-topsheet capacity of at least 0.2 g/in2 (1.3 g/cm2) when submitted to the Trans Topsheet Capacity test as described in EP-A-0,706,546, which is incorporated herein by reference.

The backsheet 24 is substantially impervious to liquids (e.g., urine) and is preferably manufactured from a thin plastic film, although other flexible liquid impervious materials may also be used. As used herein, the term "flexible" refers to materials which are compliant and will readily conform to the general shape and contours of the wearer. The backsheet is intended to prevent the exudates absorbed and contained in the absorbent core from wetting articles which contact the diaper such as bed sheets and undergarments. The backsheet may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mils) to about 0.051 mm (2.0 mils).

In a particular embodiment of the present invention, at least a portion of the backsheet is subjected to mechanical stretching in order to provide both a "zero strain" stretch laminate that forms the elastic side panels and, if desired, to prestrain the portion of the backsheet coinciding with the elastic waist feature or any other elastic feature. For this, the backsheet is preferably elongatable, most preferably drawable, but not necessarily elastomeric, so that the backsheet will, upon mechanical stretching, be at least to a degree permanently elongated such that it will not fully return to its original undistorted configuration. In preferred embodiments, the backsheet can be subjected to mechanical stretching without undue rupturing or tearing. Therefore, it is preferred that the backsheet have an ultimate elongation to break of at least about 400% to about 700% in the cross-machine direction as measured using a method consistent with ASTM D-638. Thus, preferred polymeric films for use as such a backsheet contain a high content of linear low density polyethylene. Particularly preferred materials for the backsheet include blends comprised of about 45–90% linear low density polyethylene and about 10–55% polypropylene. Exemplary films for use as the backsheet of the present invention are manufactured by Tredegar Industries, Inc. of Terre Haute, Ind. under the designations X-8323, RR8220 blend for certain blown films, and RR5475 blend for certain cast films.

The backsheet 24 can be embossed (typically, to a caliper of about 0.127 mm (5.5 mils)) and/or matte finished to provide a more clothlike appearance. Further, the backsheet may permit vapors to escape from the absorbent core (i.e., breathable) while still preventing exudates from passing through the backsheet. Examples of vapor permeable backsheet materials include microporous films, such as available from Exxon . . . under the designation EXXAIRE® or laminates, monolithic films, such as available from Elf AtoChem under the designation PEEBAX®, or from DuPont under the designation HYTREL®, or from BF Goodrich under the designation ESTANE®, or laminates and nonwoven laminate structures.

The backsheet 24 is positioned adjacent the lower surface of the absorbent core 28 and can be joined thereto by attachment means (not shown) such as those well known in the art. Alternatively, an additional material (e.g., an additional acquisition material) may be placed between the backsheet 24 and the absorbent core 28. For example, the backsheet 24 may be secured to the absorbent core 28 or any intervening material by a uniform continuous layer of adhesive, a patterned layer of adhesive, or an array of separate lines, spirals, or spots of adhesive. Adhesives which have been found to be satisfactory are manufactured by Century Adhesives, Inc. of Columbus, Ohio and marketed as Century 5227; and by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waist-Containment Garment" which issued to. Minetola and Tucker on Mar. 4, 1986. An exemplary attachment means of an open pattern network of filaments comprises several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

The absorbent core 28 will comprise any absorbent material which is capable of distributing and/or retaining liquids such as urine and other certain body exudates, and which is capable of providing the fluid distribution/storage properties which define the present invention. While absorbent core 28 is depicted in FIG. 1 in an "I" configuration, any shape may be utilized.

Figure 2:
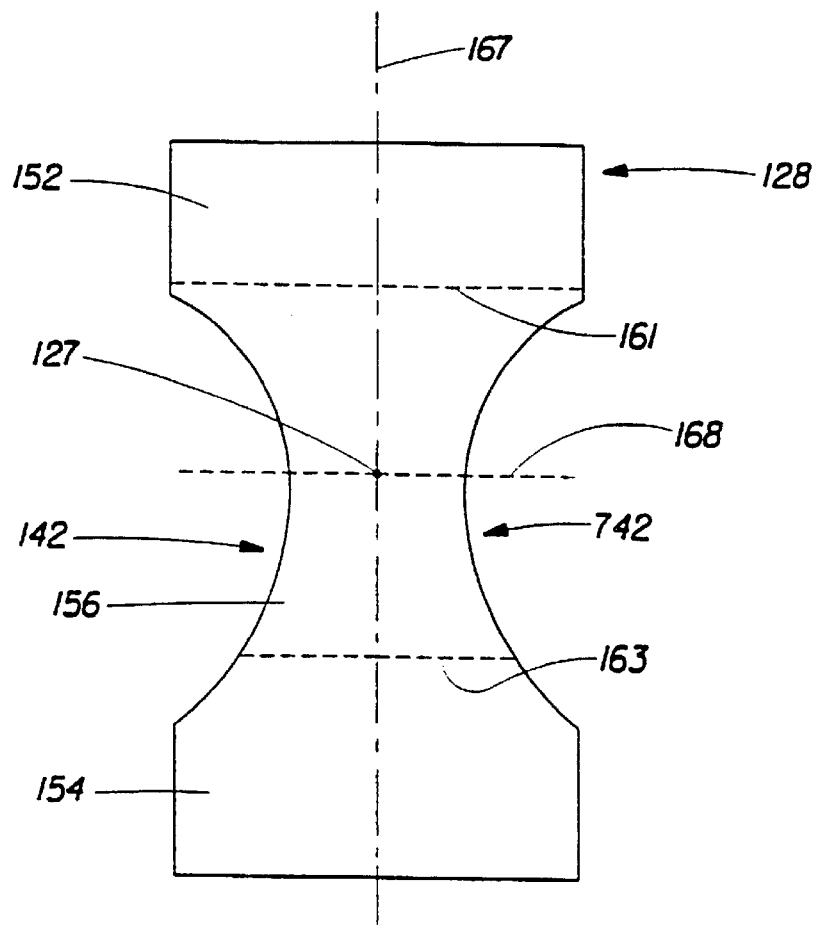
FIG. 2 is a plan view of an absorbent core of the present invention.

For example, an absorbent core 128 is shown in FIG. 2 in an "hour glass" configuration, wherein the core has arcuate cutouts in its longitudinal edges, indicated generally as 142. For illustration purposes, the crotch point is identified by item 127. (As discussed above, the crotch point of the absorbent core is extrapolated from the wearer.) As shown, the crotch point 127 generally lies on longitudinal center line 167 and on transverse line (though not the center transverse line in this embodiment) 168. The crotch region is determined by measuring forward from the crotch point a distance of 25% of the core's total length (depicted as transverse line 161) and backward from the crotch point a distance of 25% of the core's total length (depicted as transverse line 163). The crotch region 156, is the region of the core between transverse lines 161 and 163. In addition to crotch region 156, core 128 has a front region 152 and a rear region 154.

Figure 3:
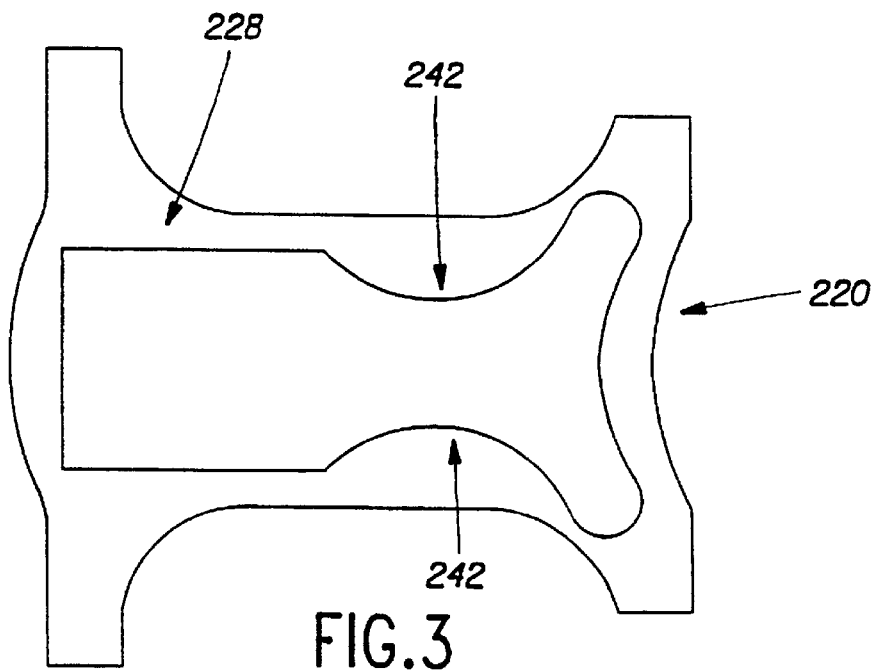
FIG. 3 is a plan view of another absorbent core of the present invention.

FIG. 3 illustrates another diaper and corresponding core configuration. In particular, diaper 220 is configured so as to fit within the low motion zone of the wearer. (A disclosure of low motion articles and corresponding cores are described in detail in U.S. Pat. No. 5,358,500 to LaVon et al., the disclosure of which is incorporated herein by reference.) The absorbent core, depicted generally as 228, is also configured so as to fit within the low motion zone of the wearer.

Figure 4:
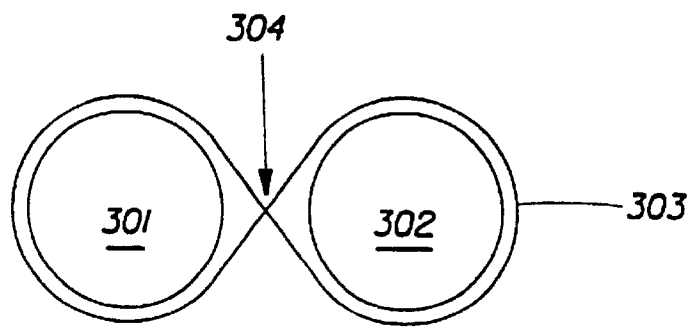
FIG. 4 illustrates how the crotch point of a wearer, an absorbent article and the corresponding absorbent core are determined.

FIG. 4 illustrates the means for determining the crotch point of an article and its absorbent core. Referring to FIG. 4, the legs of a standing wearer are depicted cross sectionally as 301 and 302. A continuous material 303 (e.g., a string or rubberband) is twisted once and is placed around the wearer's legs at a point sufficiently close the wearer's torso such that the intersection 304 of material 303 can be extrapolated onto the article being worn. The crotch point of the core of the article is thereby determined, and the crotch region of the core is determined per the above description.

The crotch width of the absorbent core at the crotch point, when dry and when wet, is important in providing improved fit on the wearer. It is preferred that the crotch width be small, even when wetted with fluid, so that the absorbent core undergoes minimal bunching when the wearer's legs are closed. In this regard, the absorbent cores useful in the present invention will have a crotch width when dry and optionally when wet of not more than about 9 cm. Preferably, the crotch width when dry and preferably also when wet will be not more than about 7 cm, still more preferably not more than about 5 cm, and yet more preferably less than 3 cm. Wet crotch width can be measured following the Curved Acquisition test described hereinafter. As it pertains to the issue of bunching during wear, crotch width may be more relevant than cross sectional area at the core's crotch point. Also in this context, the narrowest dimension in the transverse dimension is considered to be the crotch width layer.

It follows that a reduction in the crotch width of an absorbent core with a uniform capacity per unit surface area necessarily reduces the amount of material and capacity in the liquid deposition zone. Prior attempts to improve fit by reducing width in the crotch region did so by increasing capacity per unit surface area so as to maintain the necessary capacity in the crotch region. Such prior attempts utilized additional fiber in the crotch region for liquid absorption and in some instances additional hydrogel-forming polymers for liquid storage. These approaches therefore result in thicker absorbent cores, particularly in the crotch region, which in turn have a negative impact on bulk both dry and wet. In direct contrast, the present invention is intended to move the fluid deposited in the crotch region away from that region. This is reflected in the reduced level of fluid storage in the crotch region of the absorbent core. As such, in a preferred embodiment of the present invention, the crotch region of the absorbent core will comprise material(s) that function to distribute fluids away from the crotch region. While fluid distribution is an important function of the core's crotch region material, it is within the scope of the invention to include materials in the crotch region whose primary function is the storage of fluids, so long as the requisite level of storage in the crotch region is not exceeded.

Although one of the aspects of the present invention is to reduce the stored liquid in the crotch, this does not necessarily result in a reduction in the thickness of the structure. The narrow crotch width of the absorbent core in conjunction with the lack of storage in the crotch region, need for increased distribution out of the crotch, results in a need for the absorbent core to temporarily store the various liquid loadings until the liquid can be partitioned and distributed to the storage layer. It follows for materials previously disclosed such as those in Duncan et al. that to compensate for the need for temporary storage of fluid in a narrow crotch design of the present invention will result in the structure in the crotch becoming substantially thicker to provide the necessary acquisition/distribution capacity. Therefore, it is intended that the present invention provide absorbent articles that are thin in the crotch when dry, preferably less than 10 mm, more preferably less than 8 mm, most preferably less than 5 mm. Furthermore it is intended that the present invention provide absorbent articles with an Actual Wet Crotch Caliper, AWCC, as determined follwing the Curved Acquisition test as described hereinafter, that is less than 20 mm, preferably less than 15 mm, more preferably less than 10 mm, and still more preferably less than 5 mm. To further enhance overall fit and comfort of the article it is preferred that the AWCC of the absorbent article is less than the Saturated Crotch Caliper, SCC, of the article. The SCC reflects the core condition when loaded with a relatively large gush. In this state the material swells to absorb the liquid. As the material is dewatered, the capillary forces within the structure cause the structure to recollapse thereby providing a lower caliper, AWCC, than the SCC. Certain HIPE based open celled polymeric foam structures demonstrate this recollapse property. It is therefore preferred that the AWCC of the absorbent article be less than 90% of the SCC, preferably less than 50%, more preferably less than 25%. It is further desired that the AWCC also be less than the caliper of the absorbent article in either one or both of the waist regions when measured immediately adjacent said crotch region as detailed in the TEST METHODS section.

In combination with the requisite crotch width parameters, the absorbent articles of the present invention will comprise an absorbent core that retains less than about 40% of the absorbent core's total capacity in the crotch region of the core. Of course, the storage of smaller amounts of fluids in the core's crotch region, relative to the front/rear waist regions of the core, is a reflection of the ability of the core materials to move fluid out of the crotch region during wear, and thereby improve fit and wearer comfort. In this regard, the absorbent cores useful in the present invention will preferably retain less than about 25%, more preferably less than about 15%, still more preferably from 0% to about 10%, of the core's total capacity at equilibrium in the core's crotch region. In certain embodiments, the absorbent core will be constructed such that a majority of the absorbed fluid (i.e., greater than 50%) will ultimately be stored behind the crotch point of the core. Preferably, at least 55%, more preferably 65% and still more preferably 80% of the absorbent core's total absorbent capacity will be behind the core's crotch point. A method for determining total core absorbent capacity and percent capacity of the core crotch region is described in the Test Methods section below.

In addition to crotch width and liquid storage in the crotch, another key factor contributing to comfort and fit is thickness or bulk of the absorbent core itself. Although some of the art discloses cores with relatively thin dry calipers, for example U.S. Pat. No. 5,089,423 to Pieniak, et al. which discloses a wide core with a low cross sectional area this will only result in a relatively thin dry caliper, Pieniak et al. also discloses that at least 60% of the total absorbed fluid is retained in the diaper impact zone. Therefore, the Pieniak designs do not yield absorbent structures that are also thin once wetted. Therefore, it is the intent of the present invention to provide an absorbent structure that is thin when dry, less than about 8 mm, preferably less than 5 mm and more preferably less than 3 mm when measured at the crotch point, and also relatively thin when wet, less than 20 mm, more preferably less than 15 mm, still more preferably less than 10 mm and even more preferably less than 5 mm when measured at the crotch point. It is further intended that the caliper of the wet absorbent article at the crotch point will be less than the caliper of the wet article measured in the front or rear waist regions immediately adjacent said crotch region.

Duncan, et al. U.S. Pat. No. 3,592,194 discloses an absorbent structure with a single layer of material in the central section and multiple layers in the extremities. Although Duncan provides a relatively thin central section, the fluid handling mechanism disclosed by Duncan involves flooding of the central section. This central section becomes saturated or nearly saturated upon loading and the liquid is distributed horizontally by mechanical, compressive, forces on the absorbent core itself. A saturated or nearly saturated absorbent core as disclosed in Duncan when exposed to compressive mechanical forces such as the baby sitting will result in extremely high rewet values. It is a further intention of the invention that the Post Curved Acquisition Collage Rewet value in the crotch region will be less than 180 mg, preferably less than 150 mg, more preferably less than 100 mg and still more preferably less than 50 mg. These values apply for absorbent cores with a 90 mm or wider width crotch whereon the 90 mm diameter test apparatus can be applied. For absorbent cores with narrower crotch widths a reduction in diameter of the test apparatus to match the crotch width is required. Additionally, a reduction in the applied weight is also required to maintain an equal pressure per unit area between the different measurements.

Acquisition Material

A desirable source of hydrophilic fibers for use in the present invention as the acquisition material is chemically stiffened cellulosic fibers. As used herein, the term "chemically stiffened cellulosic fibers" means cellulosic fibers that have been stiffened by chemical means to increase the stiffness of the fibers under both dry and wet conditions. Such means can include the addition of a chemical stiffening agent that, for example, coats and/or impregnates the fibers. Such means can also include the stiffening of the fibers by altering the chemical structure, e.g., by cross linking polymer chains.

Polymeric stiffening agents that can coat or impregnate the cellulosic fibers include: cationic modified starches having nitrogen-containing groups (e.g., amino groups) such as those available from National Starch and Chemical Corp., Bridgewater, N.J., USA; latexes; wet strength resins such as polyamide-epichlorohydrin resin (e.g., Kymene® 557H, Hercules, Inc. Wilmington, Del. USA), polyacrylamide resins described, for example, in U.S. Pat. No. 3,556,932 (Coscia et al), issued Jan. 19, 1971; commercially available polyacrylamides marketed by American Cyanamid Co., Stamford, Conn, USA, under the tradename Parez® 631 NC; urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

These fibers can also be stiffened by chemical reaction. For example, crosslinking agents can be applied to the fibers that, subsequent to application, are caused to chemically form intrafiber crosslink bonds. These crosslink bonds can increase the stiffness of the fibers. While the utilization of intrafiber crosslink bonds to chemically stiffen the fiber is preferred, it is not meant to exclude other types of reactions for chemical stiffening of the fibers.

Fibers stiffened by crosslink bonds in individualized form (i.e., the individualized stiffened fibers, as well as processes for their preparation) are disclosed, for example, in U.S. Pat. No. 3,224,926 (Bemardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al.), issued Jul. 12, 1977. More preferred stiffened fibers are disclosed in U.S. Pat. No. 4,822,453 (Dean et al), issued Apr. 18, 1989; U.S. Pat. No. 4,888,093 (Dean et al), issued Dec. 19, 1989; U.S. Pat. No. 4,898,642 (Moore et al), issued Feb. 6, 1990; and U.S. Pat. No. 5,137,537 (Herrow et al), issued Aug. 11, 1992, all of which are incorporated by reference.

In the more preferred stiffened fibers, chemical processing includes intrafiber crosslinking with crosslinking agents while such fibers are in a relatively dehydrated, defibrated (i.e., individualized), twisted, curled condition. Suitable chemical stiffening agents are typically monomeric crosslinking agents including, but not limited to, $C_2$–$C_8$ dialdehyde, $C_2$–$C_8$ monoaldehydes having an acid functionality, and especially $C_2$–$C_9$ polycarboxylic acids. These compounds are capable of reacting with at least two hydroxyl groups in a single cellulose chain or on proximately located cellulose chains in a single fiber. Specific examples of such crosslinking agents include, but are not limited to, glutaraldehyde, glyoxal, formaldehyde, glyoxylic acid, oxydisuccinic acid and citric acid.

The effect of crosslinking under these conditions is to form fibers that are stiffened and which tend to retain their twisted, curled configuration during use. Such fibers, and processes for making them, are described in the above incorporated patents.

The preferred stiffened fibers that are twisted and curled can be quantified by referencing both a fiber "twist count" and a fiber "curl factor". As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°. The number of twist nodes in a certain length of fibers (i.e., the twist count) is directly indicative of the degree of fiber twist, which is a physical parameter of the fiber. The procedures for determining twist nodes and total twist count are described in U.S. Pat. No. 4,898,642.

The preferred stiffened fibers will have an average dry fiber twist count of at least about 2.7, preferably at least about 4.5 twist, nodes per millimeter. Furthermore, the average wet fiber twist count of these fibers should preferably be at least about 1.8, preferably at least about 3.0, and should also preferably be at least about 0.5 twist nodes per millimeter less than the average dry fiber twist count. Even more preferably, the average dry fiber twist count should be at least about 5.5 twist nodes per millimeter, and the average wet fiber twist count should be at least about 4.0 twist nodes per millimeter and should also be at least 1.0 twist nodes per millimeter less than its average dry fiber twist count. Most preferably, the average dry fiber twist count should be at least about 6.5 twist nodes per millimeter, and the average wet fiber twist count should be at least about 5.0 twist nodes per millimeter and should also be at least 1.0 twist nodes per millimeter less than the average dry fiber twist count.

In addition to being twisted, these preferred stiffened fibers are also curled. Fiber curl can be described as the fractional shortening of the fiber due to kinks, twists, and/or bends in the fiber. For the purposes of the present invention, fiber curl is measured in terms of a two dimensional plane. The extent of fiber curling can be quantified by referencing a fiber curl factor. The fiber curl factor, a two dimensional measurement of curl, is determined by viewing the fiber in a two dimensional plane.

To determine curl factor, the projected length of the fiber as the longest dimension of a two dimensional rectangle encompassing the fiber, $L_R$, and the actual length of the fiber, $L_A$, are both measured. The fiber curl factor can then be calculated from the following equation:

$$\text{Curl Factor} = (L_A/L_R) - 1.$$

An image analysis method that can be utilized to measure $L_R$ and $L_A$ is described in U.S. Pat. No. 4,898,642. Preferably the stiffened fibers will have a curl factor of at least about 0.30, and more preferably will have a curl factor of at least about 0.50.

These chemically stiffened cellulosic fibers have certain properties that make them particularly useful in certain absorbent members according to the present invention, relative to unstiffened cellulosic fibers. In addition to being hydrophilic, these stiffened fibers have unique combinations of stiffness and resiliency. This allows thermally bonded absorbent structures made with these fibers to maintain high levels of absorptive capacity, and to exhibit high levels of resiliency and an expansionary responsiveness to wetting. In particular, the resiliency of these stiffened fibers enables the absorbent member to better maintain its capillary structure in the presence of both fluid and compressive forces normally encountered during use and are thus more resistant to collapse.

A key attribute of such acquisition materials is the Medium Desorption Pressure, MDP, of the material. The MDP is a measure of the capillary pressure that is required to dewater the acquisition structure to 50% of its capacity at 0 cm capillary suction height as derived from the Capillary Sorption test, herein after described. Generally, a relatively lower MDP is preferred. The lower MDP allows the distribution material to more efficiently drain the acquisition material. The reduced desorption pressure also allows the distribution material to utilize more of its capillary suction to distribute liquid to the storage material. Without wishing to be bound by theory, a given distribution material will have a definable capillary suction. The ability of the distribution material to move liquid vertically via capillary forces will be directly impacted by the opposing capillary forces associated with the desorption of the acquisition material. Minimizing these capillary forces, desorption of the acquisition layer, will positively impact the performance of the distribution material. Therefore, it is the intent to have an acquisition material with an MDP corresponding to a height of less than 18 cm, preferably less than 15 cm and more preferably less than 10 cm. However, the primary acquisition material must also have adequate capillary absorption suction in order to drain the topsheet layer and to temporarily hold liquid until the liquid can be partitioned away by the other core components. Therefore, preferred materials should have a minimum MDP which should correspond to a height of greater than 5 cm.

The acquisition materials of the present invention are not only required to absorb liquid and temporarily hold the liquid until it is partitioned to the distribution layer, the acquisition materials are also required to acquire the liquid relatively rapidly. The absorbent articles of the present invention comprising said acquisition materials will preferably have an initial acquisition rate of at least 5 ml/sec, preferably at least 10 ml/sec and most preferably at least 15 ml/sec. These rates are for a 75 ml gush loading in a Maxi size product. Furthermore it is important that the absorbent articles of the present invention comprising said acquisition materials also have a relatively fast fourth gush acquisition rate. Therefore it is preferred that the fourth gush acquisition rate be at least 0.25 ml/sec, preferably at least 0.75 ml/sec, more preferably at least 1.5 ml/sec and most preferably at least 3 ml/sec. These data are measured by the Curved Acquisition Test Method, described below.

Distribution Material

As discussed above, the absorbent core will comprise a material which functions to distribute fluid out of the core's crotch region. Vertical wicking, i.e., fluid wicking in a direction opposite from gravitational force, is an especially desirable performance attribute for the distribution material. The distribution material will frequently be utilized in absorbent articles in a manner such that fluid to be absorbed must be moved within the article from a relatively lower position to a relatively higher position within the absorbent core of the article. Accordingly, the ability of these materials to wick fluid against gravitational forces is particularly relevant to their functioning as absorbent materials in the present absorbent articles.

As described previously the diaper structures disclosed in Bernardin lose a substantial percentage of their gram/gram capacity relative to vertically wicked height, especially at heights of 13.5 cm or greater. Table 6 from Bernardin et al., shows that the capacity of the combined absorbent in the diaper has a grams fluid/gram absorbent value at 0.0 cm of 9.9 g/g and a gram/gram absorbent capacity value at 13.5 cm of 2.6 g/g. This data reflects a retained gram/gram capacity at 13.5 cm of less than 30% of the gram/gram capacity at 0.0 cm. When structures according to the present invention are subjected to the Whole Diaper Vertical Wicking Test, the grams fluid/gram absorbent reached in the crotch region is significantly enhanced by exhibiting a gram/gram capacity at 13.5 cm that is at least 50% of the gram/gram capacity at 0 cm, preferably 75% more preferably 125% and most preferably 200%. Furthermore, such absorbent articles should have a gram/gram capacity at 18 cm that is at least 30% of the gram/gram capacity at 0 cm, preferably at least 50%, more preferably at least 100% and most preferably at least 150%.

The wicking characteristics that are particularly relevant for fluid distribution are: A) the rate of vertical wicking of fluid through the distribution material; and B) the absorbent capacity of the distribution material at specific referenced wicking heights. Another important property of distribution material is its ability to drain (partition) fluid from competing absorbent structures (e.g., acquisition materials) with which the material can be in contact.

Vertical wicking rate is determined by measuring the time taken for a colored test liquid (e.g., synthetic urine) in a reservoir to wick a vertical distance of 5 cm through a test strip of material of specified size. The vertical wicking procedure is described in greater detail in the TEST METHODS section of U.S. Pat. No. 5,387,207, but is performed at 31° C., instead of 37° C. To be especially useful in absorbent articles for absorbing urine, the distribution material will wick synthetic urine (65±5 dynes/cm) to a height of 5 cm in no more than about 30 minutes. More preferably, the distribution material will wick synthetic urine to a height of 5 cm in no more than about 15 minutes, still more preferably in no more than about 5 minutes. In another preferred embodiment, the distribution material will wick synthetic urine to a height of 12 cm in no more than about 2 minutes.

The vertical wicking absorbent capacity test measures the amount of test fluid per gram of distribution material that is held within each one inch (2.54 cm) vertical section of the same standard size sample used in the vertical wicking test. Such a determination is generally made after the sample has been allowed to vertically wick test fluid to equilibrium for some 24 hours. The vertical wicking absorbent capacity test is described in greater detail in the TEST METHODS section of U.S. Pat. No. 5,387,207.

In a preferred embodiment, the absorbent core useful in the articles of the present invention will comprise a fluid distribution material having a vertical wicking capacity of at least about 10 g/g, preferably at least about 35 g/g, still more preferably at least about 60 g/g, at a height of 2 cm. In another preferred embodiment, the absorbent core will comprise a distribution material having a vertical wicking absorbent capacity at a height of 20 cm of at least about 5 g/g, preferably at least about 20 g/g, more preferably at least about 40 g/g, still more preferably at least about 60 g/g. In another preferred embodiment, the fluid distribution material of the absorbent core will have a vertical wicking absorbent capacity at a height of 25 cm of at least about 2 g/g, preferably at least about 20 g/g, more preferably at least about 40 g/g. In another preferred embodiment, the fluid distribution material will have a vertical wicking absorbent capacity at a height of 30 cm of at least about 0.5 g/g, preferably at least about 10 g/g, more preferably at least about 20 g/g, still more preferably at least about 30 g/g.

In one embodiment, the absorbent core will comprise the same material in the front and rear of the core as is contained in the crotch region thereof. That is, the distribution material will also be suitable for fluid storage. Alternatively, the core can contain a distinct storage material in the front and/or rear waist regions of the core and a different material extending through the length of the crotch region for distribution. This storage material may then desorb the distribution materials.

A preferred absorbent material for providing the requisite distribution properties is an open-celled absorbent polymeric foam material that is derived by polymerizing a High Internal Phase Water-in-Oil Emulsion (hereafter referred to a HIPE). Such polymeric foams may be formed to provide the requisite storage properties, as well as the requisite distribution properties. Where distinct storage materials are included in the front and rear sections of the core, the polymeric distribution foams will preferably exhibit desorption properties that allow the storage core components to partition away fluid. It is desirable that these components keep the wearer's skin dry, even in "gush" situations and even when subjected to a compressive load; are soft, flexible and comfortable to the wearer of the absorbent article; and have relatively high capacity for fluid so as to provide diapers and other absorbent articles that efficiently utilize such core components.

HIPE-derived foams which provide both the requisite distribution and storage properties for use herein are described in copending U.S. patent application Ser. No. 08/563,866 (DesMarais et al.), filed Nov. 25, 1995 (hereafter referred to as "'866 application"); U.S. Pat. No. 5,387,207 (Dyer et al.), issued Feb. 7, 1995; and U.S. Pat. 5,260,345 (DesMarais et al.), issued Nov. 9, 1993; the disclosure of each of which is hereby incorporated by reference.

Polymeric foams useful as the distribution material in the present invention are those which are relatively open-celled. This means a significant proportion of the individual cells of the foam are in communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 1 and 2 in the '866 application. As used herein, a foam material is "open-celled" if at least 80% of the cells in the foam structure that are at least 1 $\mu$m in size are in fluid communication with at least one adjacent cell.

In addition to being open-celled, these polymeric foams are sufficiently hydrophilic to permit the foam to absorb aqueous fluids in the amounts specified hereafter. The internal surfaces of the foam structures are rendered hydrophilic by residual hydrophilizing surfactants left in the foam structure after polymerization, or by selected post-polymerization foam treatment procedures.

The polymeric foams can be prepared in the form of collapsed (i.e. unexpanded), polymeric foams that, upon contact with aqueous fluids, expand and absorb such fluids. See, for example, copending U.S. patent application Ser. No. 08/563,866 and U.S. Pat. No. 5,387,207. These collapsed polymeric foams are usually obtained by expressing the water phase from the polymerized HIPE foam through compressive forces, and/or thermal drying and/or vacuum dewatering. After compression, and/or thermal drying/vacuum dewatering, the polymeric foam is in a collapsed, or unexpanded state. Non-collapsible foams, such as those described copending U.S. patent application Ser. No. 08/542,497 and U.S. Pat. No. 5,260,345 are also useful as the distribution material.

An important parameter of these foams is their glass transition temperature. The Tg represents the midpoint of the transition between the glassy and rubbery states of the polymer. Foams that have a higher Tg than the temperature of use can be very strong but will also be very rigid and potentially prone to fracture. When such foams are collapsible, they also typically take a long time to recover to the expanded state when wetted with aqueous fluids colder than the Tg of the polymer after having been stored in the collapsed state for prolonged periods. The desired combination of mechanical properties, specifically strength and resilience, typically necessitates a fairly selective range of monomer types and levels to achieve these desired properties.

It has been found that the specific surface area per foam volume of the polymeric foam is particularly useful for empirically defining foam structures that will remain in a collapsed state. Furthermore, this property is important to the foam's ability to provide the vertical wicking capacities discussed herein. See U.S. Pat. No. 5,387,207, where specific surface area per foam volume is discussed in detail.

"Specific surface area per foam volume" refers to the capillary suction specific surface area of the foam structure times its foam density in the expanded state. Polymeric foams having specific surface area per foam volume values of at least about 0.025 m$^2$/cm$^3$, more preferably at least about 0.05 m$^2$/cm$^3$, most preferably at least about 0.07 m$^2$/cm$^3$, have been found empirically to remain in a collapsed state, and are therefore preferred herein.

Another important property of the absorbent polymer foams useful herein is their free absorbent capacity. "Free absorbent capacity" is the total amount of test fluid (synthetic urine) which a given foam sample will absorb into its cellular structure per unit mass of solid material in the sample. To be especially useful in the absorbent articles of the present invention, the absorbent foams should have a free absorbent capacity of from about 15 to about 100 ml, preferably from about 25 to about 75 ml of synthetic urine per gram of dry foam material. The procedure for determining the free absorbent capacity of the foam is described in the TEST METHODS section of the '866 application.

Upon exposure to aqueous fluids, collapsible foams useful herein expand and absorb the fluids. When these foams are compressively dewatered to a thickness of about ⅙ (17%) or less of their fully expanded thickness, they remain in a very thin state, with a concomitant increase in storage efficiency and flexibility. This is attributable to the low density of the expanded foams. The "expansion factor" for these foams is at least about 4×, i.e. the thickness of the foam in its expanded state is at least about 4 times the thickness of the foam in its collapsed state. The collapsed foams preferably have an expansion factor in the range of from about 4× to about 10×.

For the purposes of the present invention, the relationship between expanded and collapsed thickness for compressively dewatered collapsible foams can be empirically approximated from the following equation:

$$\text{thickness}_{expanded} = \text{thickness}_{collapsed} \times 0.133 \times \text{W:O ratio}$$

where "thickness$_{expanded}$" is the thickness of the foam in its expanded state;

"thickness$_{collapsed}$" is the thickness of the foam in its collapsed state;

and "W:O ratio" is the water-to-oil ratio of the high internal phase emulsion from which the foam is made. Thus, a typical foam made from an emulsion with water-to-oil ratio of 60:1 would have a predicted expansion factor of 8.0, i.e., an expanded thickness 8 times the collapsed thickness of the foam. The procedure for measuring the expansion factor is described in the Test Method section of the '866 application.

An important mechanical feature of the absorbent polymeric foams useful in the present invention, whether collapsible or non-collapsible, is their strength in their expanded state, as determined by its resistance to compression deflection (RTCD). The RTCD exhibited by the foams is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as absorbents in absorbent articles such as diapers, the foams of the present invention must be suitably resistant to deformation or compression by forces encountered in use when such absorbent materials are engaged in the absorption and retention of fluids. Foams which do not possess sufficient foam strength in terms of RTCD may be able to acquire and store acceptable amounts of body fluid under no-load conditions but will too easily give up such fluid under the compressive stress caused by the motion and activity of the user of the absorbent articles that contain the foam.

The RTCD exhibited by the polymeric foams useful herein can be quantified by determining the amount of strain produced in a sample of saturated foam held under a certain confining pressure for a specified temperature and period of time. The method for carrying out this particular type of test is described in the TEST METHODS section of the '866 application. Foams useful as absorbents are those which exhibit a RTCD such that a confining pressure of 5.1 kPa produces a strain of typically about 50% or less compression of the foam structure when it has been saturated to its free absorbent capacity with synthetic urine having a surface tension of 65 ±5 mN/m. Preferably the strain produced under such conditions will be in the range from about 2 to about 25%, more preferably from about 2 to about 15%, most preferably from about 2 to about 10%.

Although the foam based materials of the present invention function well for distribution and/or storage, the fact that these materials are compressible can lead to release or fluid due to compression. This fluid release can potentially result in an increase in rewet from the absorbent core. This rewet can be overcome to some extent by making the foam structures disclosed above very strong, e.g. 2% compression. These materials, however, may be stiff in use and may negatively impact fit and comfort. In order to balance material strength and comfort, the foam material preferably has some degree of compressibility and therefore liquid release under pressure. To overcome this issue, the incorporation of rewet barriers or layers has been introduced as part of the invention. These rewet barriers are intended to provide a separation layer capable of accepting and even storing the liquid released from the lower storage or distribution regions. Examples of effective rewet barriers include Super absorbent Hydrogel materials, polymeric foam materials or combinations of polymeric foam materials and Hydrogel materials. The effectiveness of the various rewet barriers can be assessed by conducting the PCACORM rewet method with the barrier layer in place and then without the barrier layer. The relative difference can be interpreted as the relative effectiveness of the rewet barrier. The PCACORM rewet value obtained with the absorbent article with the rewet barrier will be lower than the rewet value of the article without the rewet barrier. Preferably the rewet value of the article with the rewet barrier will be less than 70% of the value obtained without the barrier, more preferably less than 50% and even more preferably less than 20%.

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

A number of techniques are available for determining the average cell size of foams. The most useful technique, however, for determining cell size in foams involves a simple measurement based on the scanning electron photomicrograph of a foam sample. The cell size measurements given herein are based on the number average cell size of the foam in its expanded state. The foams useful as absorbents for aqueous fluids in accordance with the present invention will preferably have a number average cell size of about 50 $\mu$m or less, and typically from about 5 to about 35 $\mu$m.

"Foam density" (i.e., in grams of foam per cubic centimeter of foam volume in air) is specified herein on a dry basis. The amount of absorbed water-soluble residual materials, e.g., residual salts and liquid left in the foam, for example, after HIPE polymerization, washing and/or hydrophilization, is disregarded in calculating and expressing foam density. Foam density does include, however, other water-insoluble residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure described more fully in the TEST METHODS section of U.S. Pat. No. 5,387,207 is one method that can be employed for density determination. In its collapsed state, polymeric foams of the present invention useful as absorbents have dry basis density values in the range of from about 0.1 to about 0.2 g/cc, preferably from about 0.11 to about 0.15 g/cc, and most preferably from about 0.12 to about 0.14 g/cc. In its expanded state, polymeric foams of the present invention useful as absorbents have dry basis density values in the range of from about 0.010 to about 0.040 g/cm$^3$, preferably from about 0.013 to about 0.030 g/cm$^3$.

Suitable absorbent foams will in general exhibit especially desirable and useful aqueous fluid handling and absorbency characteristics. In particular, when the foam is used as the primary distribution material in an absorbent core of the present invention, the ability to move fluid from the crotch region of the core to the front and/or rear regions of the core is important.

Another important property of useful absorbent foams according to the present invention is their capillary absorption pressure. Capillary absorption pressure refers to the ability of the foam to wick fluid vertically. [See P. K. Chatterjee and H. V. Nguyen in "Absorbency," Textile Science and Technology, Vol. 7; P. K. Chatterjee, Ed.; Elsevier: Amsterdam, 1985; Chapter 2.] For the purposes of the present invention, the capillary absorption pressure of interest is the hydrostatic head at which the vertically wicked fluid loading is 50% of the free absorbent capacity under equilibrium conditions at 31° C. The hydrostatic head is represented by a column of fluid (e.g., synthetic urine) of height h. To be especially useful in absorbent articles for absorbing aqueous fluids, the preferred absorbent foams useful herein will generally have a capillary absorption pressure of at least about 24 cm. (Foams useful herein preferably have an absorption pressure of at least about 30 cm, more preferably at least about 40 cm.)

Another preferred material for use specifically as the distribution material in the crotch region of the present articles is described in copending U.S. patent application Ser. No. 08/633,630 (G. Seger et al.), filed Apr. 17, 1996, which is incorporated by reference herein. These fiber-based distribution materials, referred to therein as "fluid absorbent members", preferably comprise three basic components: chemically stiffened, twisted, and curled bulking fibers, high surface area fibers, and chemical binder additive, each of which is described in detail. The fibrous members described utilize a high surface area fiber to provide capillary pressure (or suction) to the fluid absorbent member. These high surface area fibers are generally low diameter and can be highly conformable. They provide the fibrous member with capillary pressure well in excess of the capillary pressure found in the bulk-providing chemically stiffened, twisted, and curled fibers (unrefined) alone. Preferred fibers for this high surface area application are the eucalyptus family of wood pulp fibers. Particularly suitable eucalyptus fibers include those of the eucalyptus grandis species.

The fibrous members preferably comprise from about 80% to about 95% of the chemically stiffened, twisted, and curled fibers, from about 3% to about 20% of a high surface area fiber, and from 0% to about 5% of a chemical additive binding means for increasing physical integrity of the web. (All percentages refer to weight percentages based on total dry web weight.) Preferably, the fluid absorbent members will comprise between about 80% and about 90% of chemically stiffened, twisted, and curled fibers, between about 8% and about 18% of a high surface area fiber (hereafter described), and between about 0.25% and about 2% of a chemical additive binding means. More preferably, the fluid absorbent members comprise about 88% chemically stiffened, twisted, and curled fibers, about 10% high surface area fibers, and about 2% chemical binding means.

In addition to the use of a chemical binding means, fluid absorbent members may also benefit from the integration of a thermally bonded polymer micro web in the material. This micro-web is formed by the polymer bonding fibers (such as Hoechst-Celanese Copolyolefin Bicomponent fiber and the like) strongly bonding at fiber intersections. In these embodiments, the thermoplastic binding material provides bond sites at intersections of the binding fibers with either other binding fibers, chemically stiffened, twisted, and curled cellulosic fibers, or high surface area fibers. Such thermally bonded webs can, in general, be made by forming a web comprising the stiffened cellulosic fibers and thermoplastic fibers, which are preferably evenly distributed throughout. The thermoplastic fibrous material can be intermixed with the stiffened cellulosic fibers and fine fibers in the aqueous slurry prior to web formation. Once formed, the web is thermally bonded by heating the web until the thermoplastic portion of the fibers melt. Specific non-limiting examples of suitable fibrous materials include polyester hot melt fibers (KODEL 410), bicomponent fibers, tricomponent fibers, mixtures thereof, and the like.

Suitable fibrous fluid distribution materials as described above can be further modified by being mechanically treated, such as described in EP-A-0.810.078, which is incorporated herein by reference.

Storage Materials

In those embodiments where the distribution material is not particularly suitable for storage of absorbed fluids, the absorbent core will also comprise a material, or combination of materials, whose primary function is the storage of absorbed fluids. The fluid storage material acts to store body exudates away from the wearer's body so as to leave the wearer with a feeling of dryness. The storage materials are maintained in fluid contact with the distribution material such that urine or other aqueous body fluids absorbed by the distribution material can be desorbed by the fluid storage material. When the storage materials are positioned in the front and/or rear regions of the absorbent core, the core provides fit benefits by storing a majority of the absorbed fluid away from the article's crotch region.

Any material capable of partitioning fluid from the distribution material may be utilized as the storage material. For example, the storage material may comprise hydrogel-forming polymers that are water-insoluble, but water-swellable and are capable of absorbing large quantities of fluids. Such polymers are commonly referred to as "hydrocolloids" or "superabsorbent" materials, and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, hydrogel-forming absorbent polymers useful herein have a multiplicity of anionic, functional groups, such as sulfonic acid, and more typically carboxy groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the hydrogel-forming absorbent polymers. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, α-chloroacrylic acid, a-cyanoacrylic acid, βmethylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use herein are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e. poly (sodium acrylate/acrylic acid)). Network crosslinking renders the polymer substantially water-insoluble and, in part, determines the absorptive capacity and extractable polymer content characteristics of the hydrogel-forming absorbent polymers. Processes for network crosslinking these polymers and typical network crosslinking agents are described in greater detail in U.S. Pat. No. 4,076,663.

Hydrogel-forming polymers may optionally be combined with fibrous materials to form the storage material. The fibrous materials facilitate, inter alia, uptake of fluid by the hydrogel-forming polymer. Nonetheless, it may be preferred to use relatively high concentrations of hydrogel-forming polymer, while at the same time avoiding the gel blocking phenomena exhibited by many hydrogel-forming polymers. The use of high concentration hydrogel-forming polymers is described in detail in U.S. Pat. No. 5,599,335 (Goldman et al.) and U.S. Pat. No. 5,562,646 (Goldman et al.), both of which are incorporated by reference herein.

Storage materials comprising hydrogel-forming polymers can also comprise fibrous materials to form fibrous web or fibrous matrices. Fibers useful herein include those that are naturally occurring fibers (modified or unmodified), as well as synthetically made fibers. Examples of suitable unmodified/modified naturally occurring fibers include cotton, Esparto grass, bagasse, kemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyplefins such as polyethylene (e.g., PULPEX®) and polypropylene, polyamides such as nylon, polyesters such as DACRON® or KODEL®, polyurethanes, polystyrenes, and the like. The fibers used can comprise solely naturally occurring fibers, solely, synthetic fibers, or any compatible combination of naturally occurring and synthetic fibers.

The fibers used can be hydrophilic, hydrophobic or can be a combination of both hydrophilic and hydrophobic fibers. As used herein, the term "hydrophilic" describes fibers, or surfaces of fibers, that are wettable by aqueous fluids (e.g., aqueous body fluids) deposited on these fibers. Hydrophilicity and wettability are typically defined in terms of contact angle and the surface tension of the fluids and solids involved. This is discussed in detail in the American Chemical Society publication entitled *Contact Angle, Wettability and Adhesion*, edited by Robert F. Gould (Copyright 1964). A fiber, or surface of a fiber, is said to be wetted by a fluid (i.e., hydrophilic) when either the contact angle between the fluid and the fiber, or its surface, is less than 90°, or when the fluid tends to spread spontaneously across the surface of the fiber, both conditions normally co-existing. Conversely, a fiber or surface is considered to be hydrophobic if the contact angle is greater than 90° and the fluid does not spread spontaneously across the surface of the fiber.

For storage materials useful herein, the use of hydrophilic fibers is preferred. Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like. For reasons of availability and cost, cellulosic fibers, in particular wood pulp fibers, are preferred for use in the present invention.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemi-thermomechanical pulp processes. Recycled or secondary wood pulp fibers, as well as bleached and unbleached wood pulp fibers, can be used.

A preferred storage material for practicing the present invention comprises polymeric foam material derived from HIPEs. These materials will preferably have sufficient absorption pressures to desorb the distribution material, thereby providing reduced fluid storage in the crotch region of the article. However, as indicated, a single material may function as both the distribution and storage material in the present articles.

The foams described above with respect to the distribution component of the present absorbent articles are also useful as the storage component of the articles. Particularly preferred are collapsible polymeric foam materials that, upon contact with aqueous fluids (in particular aqueous body fluids such as urine), can expand and absorb these fluids. These absorbent polymeric storage foam materials comprise a hydrophilic, flexible, nonionic polymeric foam structure of interconnected open-cells as disclosed in, for example, U.S. Pat. No. 5,387,207 (Dyer et al.), issued Feb. 7, 1995, and copending U.S. patent application Ser. No. 08/563,866 (DesMarais et al.), filed Nov. 25, 1995, the disclosure of each of which is hereby incorporated by reference. As is discussed above, the foam materials useful for providing requisite fluid distribution out of the crotch region may also function to retain absorbed fluid. However, as indicated, a single material may function as both the distribution and storage material in the present articles.

The storage foam material useful in the present invention provides very low density absorbent foams. For a given expanded thickness, these lower density foams more efficiently utilize the available polymer material. As a result, the lower density absorbent foams provide an economically attractive means for achieving thinner absorbent cores for absorbent articles such as diapers, adult incontinence pads or briefs, sanitary napkins, and the like. This is achieved while providing desired absorbency and mechanical properties.

The storage absorbent members of the present invention may comprise materials that exhibit high capillary suction capacities as disclosed in Young et al. P&G case 7054. For purposes of the present disclosure, this high suction capacity is measured in terms of the member's ability to uptake liquid at high capillary heights, which are generally encountered when the member is positioned in an absorbent article. The Capillary Sorption Absorbent Capacity test (also referred to herein as the Capillary Sorption test) measures the amount of test liquid per gram of storage absorbent member that is taken up when the storage member is placed at varying heights on a capillary sorption apparatus. The Capillary Sorption test is described in greater detail in the Test Methods section below.

Young et al discloses high capillary suction capacity storage absorbent members having a capillary sorption absorbent capacity at a height of 35 cm of at least about 12 g/g, preferably at least about 14 g/g, more preferably at least about 20 g/g, still more preferably at least about 27 g/g. Typically, these storage absorbent members will have a capillary sorption absorbent capacity at a height of 35 cm of from about 12 g/g to about 60 g/g, more typically from about 14 g/g to about 50 g/g, more typically from about 20 g/g to about 40 g/g.

In another embodiment, the high capillary suction capacity storage absorbent material has a capillary sorption absorbent capacity at a height of 70 cm of at least about 7 g/g, preferably at least about 9 g/g, more preferably at least about 11 g/g, still more preferably at least about 14 g/g. Typically, these storage absorbent members will have a capillary sorption absorbent capacity at a height of 70 cm of from about 7 g/g to about 35 g/g, more typically from about 9 g/g to about 30 g/g, still more typically from about 11 g/g to about 25 g/g.

In yet another embodiment of Young et al., the high capillary suction capacity storage absorbent material has a capillary sorption absorbent capacity at a height of 120 cm of at least about 4 g/g, preferably at least about 5 g/g, more preferably at least about 7 g/g, still more preferably at least about 11 g/g. Typically, these storage absorbent members will have a capillary sorption absorbent capacity at a height of 120 cm of from about 4 g/g to about 29 g/g, more typically from about 5 g/g to about 24 g/g, still more typically from about 7 g/g to about 19 g/g.

In yet another embodiment, the high capillary suction capacity storage absorbent material has a capillary sorption absorbent capacity at a height of 200 cm of at least about 3 g/g, preferably at least about 4 g/g, more preferably at least about 6 g/g, still more preferably at least about 8 g/g. Typically, these storage absorbent members will have a capillary sorption absorbent capacity at a height of 200 cm of from about 3 g/g to about 25 g/g, more typically from about 4 g/g to about 20 g/g, still more typically from about 6 g/g to about 15 g/g.

With respect to storage absorbent members comprising osmotic absorbents and high surface area materials, in addition, or alternative, to defining the high suction capabilities of the present members in terms of capillary sorption absorbent capacity, particularly preferred members, e.g. those where the high surface area material is a polymeric foam, may be characterized by the member's ability to initially uptake liquid at high heights at relatively fast rates. High suction members that exhibit both high uptake at high suction and high initial effective uptake rates should provide superior user dryness as the extent of partitioning from other absorbent core members (e.g., acquisition or distribution materials) and its rate will be favorably improved by the high suction material. For purposes of the present disclosure, this latter property is referred to herein as the member's "initial effective uptake rate at 200 cm capillary suction height" (referred to herein as "initial effective uptake rate at 200 cm"), which is reported in units of g/g/hour. The initial effective uptake rate of a storage absorbent member is calculated by dividing the capillary suction absorbent capacity at 200 cm by the time spent at 200 cm. Capillary suction absorbent capacity and time are readily determined using the Capillary Sorption method discussed in detail in the Test Methods section below. Though not a requirement, particularly preferred storage absorbent members will have an initial effective uptake rate at 200 cm of at least about 3 g/g/hr, more preferably at least about 4 g/g/hr, and most preferably at least about 8 g/g/hr. Typically, the effective uptake rate at 200 cm will be from about 3 to about 15 g/g/hr, more typically from about 4 to about 12 g/g/hr, still more typically from about 8 to about 12 g/g/hr.

While the above minimum capillary sorption absorbent capacities are important to the absorbent members of the present invention, the members will also preferably, though not necessarily, have a capillary sorption absorbent capacity at zero head pressure (i.e., at 0 cm in the Capillary Sorption test) of at least about 15 g/g. In another preferred aspect, the absorbent members will concurrently exhibit the required g/g uptake at at least two suction heights discussed above. That is, for example, preferred storage absorbent members will have 2 or more of the following properties: (i) a capillary sorption absorbent capacity at a height of 35 cm of at least about 12 g/g, preferably at least about 14 g/g, more preferably at least about 20 g/g, still more preferably at least about 27 g/g; (ii) a capillary sorption absorbent capacity at a height of 70 cm of at least about 7 g/g, preferably at least about 9 g/g, more preferably at least about 11 g/g, still more preferably at least about 14 g/g; (iii) a capillary sorption absorbent capacity at a height of 120 cm of at least about 4 g/g, preferably at least about 5 g/g, more preferably at least about 7 g/g, still more preferably at least about 11 g/g; (iv) a capillary sorption absorbent capacity at a height of 200 cm of at least about 3 g/g, preferably at least about 4 g/g, more preferably at least about 6 g/g, still more preferably at least about 8 g/g.

In yet another aspect, storage absorbent members of the present invention can be characterized in terms of exhibiting a relatively high absorbency efficiency (hereafter referred to as "capillary absorption efficiency") at various heights, relative to the material's capacity at zero head pressure. Capillary absorption efficiency at a given suction height is determined by dividing the capillary suction absorbent capacity of the material at that given height by the capillary suction absorbent capacity of that material at zero head pressure, i.e., 0 cm. In this regard, in one aspect, the absorbent member will have a capillary sorption absorbent capacity at zero height of at least about 15 g/g, preferably at least about 20 g/g, more preferably at least about 40 g/g and most preferably about 60 g/g, and capillary absorption efficiency at a height of 120 cm of at least about 25%, preferably at least about 30%, still more preferably at least about 40%. In another aspect, the absorbent member will have a capillary sorption absorbent capacity at zero height of at least about 15 g/g, preferably at least about 20 g/g, more preferably at least about 40 g/g and most preferably at least about 60 g/g, and a capillary absorption efficiency at a height of 70 cm of at least about 30%, preferably at least about 40%, still more preferably at least about 65%. In still another aspect, the absorbent member will have a capillary sorption absorbent capacity at zero height of at least about 15 g/g, preferably about 20g/g, more preferably about 40 g/g and most preferably about 60 g/g, and a capillary absorption efficiency at a height of 35 cm of at least about 50%, preferably at least about 70%, still more preferably at least about 90%.

In another embodiment, preferred storage absorbent members of the present invention will have a relatively high medium absorption height, which is defined as the height at which the member has a capillary sorption absorbent capacity that is 50% of the capillary sorption absorbent capacity at 0 cm height. In this regard, preferred storage absorbent members will have a capillary sorption absorbent capacity at zero height of at least about 15 g/g, preferably at least about 20 g/g, more preferably at least about 40 g/g and most preferably about 60 g/g, and a medium absorption height of at least about 35 cm, more preferably at least about 40 cm, still more preferably at least about 50 cm, most preferably at least about 60 cm.

Components of the High Suction Storage Absorbent Members

Representative materials useful in preparing the storage absorbent members of the present invention are described in detail below. In one preferred embodiment, the storage absorbent member will be in the form of a high surface area hydrophilic polymeric foam. In another particularly preferred embodiment, the storage absorbent member will be in the form of a high surface area hydrophilic polymeric foam in combination with an osmotic absorbent material (e.g., a hydrogel-forming absorbent polymer). In yet another embodiment, the storage absorbent member will comprise a blend of high surface area fibers and an osmotic absorbent (e.g., a hydrogel-forming absorbent polymer).

High Surface Area Hydrophilic Polymeric Foams

As indicated, high surface area hydrophilic polymeric foams having high capillary suction capacities may be used as the primary component of the storage absorbent member, or such foams may be used in combination with an osmotic absorbent material. While the foams useful as the primary storage material (i.e., no additional materials which contribute significant absorbent capacity are used) will have many similar properties to foams that are used in combination with osmotic absorbents, there are certain foam properties that will vary depending on the specific embodiment in question. In this regard, in the discussion of specific foam properties below, where no distinction is made between foams useful as the primary storage absorbent component and those to be used in combination with an osmotic absorbent, it should be assumed the description of that foam property is applicable to both embodiments. In contrast, where different foam properties are applicable depending on the embodiment in question, descriptions for each embodiment are provided.

To the extent high surface area polymeric foams useful herein are described in terms of their physical properties, it may be necessary to perform analysis on the foam in sheet form. Thus, insofar as a foam is used in particulate form and is prepared from a previously formed sheet, physical property measurements will be conducted on the sheet foam (i.e., prior to forming particulates). Where the foam is formed in situ into particles (or beads) during the polymerization process, a similar foam (in terms of chemical composition, cell size, W:O ratio, etc.) can be formed into sheets for the purpose of making such measurements.

The high capillary suction materials described above can also be utilized as the rewet barrier material for the absorbent core structure of the present invention.

The materials utilized in the absorbent core of the present articles may be arranged in a variety of ways, so long as the requisite crotch width (when dry and when wet) and crotch region fluid retention values are not exceeded. As discussed above, to achieve both properties, it is preferred to have relatively little fluid storage in the crotch region.

Figure 5:
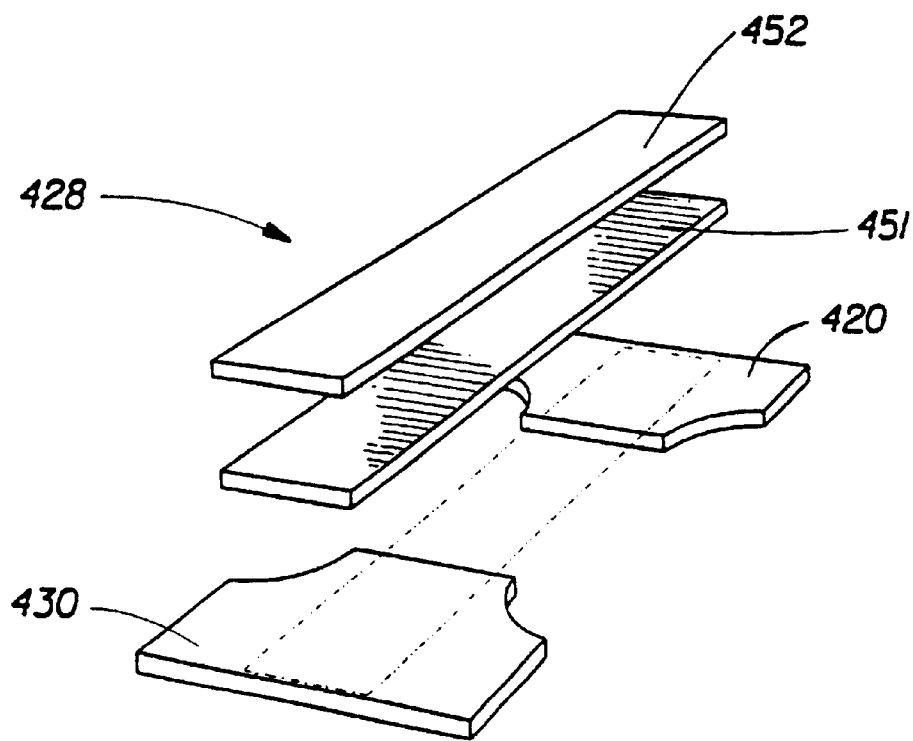
FIG. 5 is a blown apart perspective view of a multipiece absorbent core useful in the present invention.

The absorbent cores useful herein may comprise separate components for use in the crotch, front and rear portions of the absorbent core. FIG. 5 shows an exploded perspective view depicting the elements of an absorbent core 428. As depicted in FIG. 5, the absorbent core 428 comprises a front panel 420 and a back panel 430, both made of absorbent material, preferably material suitable for fluid storage. FIG. 5 further shows a center section 451 of absorbent material overlying the front and back panels 420 and 430. The material of this center section 451 comprises a fluid distribution material as described herein, or a material having requisite distribution and storage properties.

Center section 451 may comprise multiple strips of absorbent material, each having individual shape, width, length and thickness characteristics. For example, in a preferred embodiment, a relatively thin, flexible, resilient, polymeric foam strip 451 is preferably made from the same fluid distribution/storage material as the front and back panels 420 and 430. Also depicted in FIG. 5 is an acquisition material 452.

The disposable absorbent article of the present invention may also comprise a fecal management member as disclosed in Bast et al. PCT application US97/20840. Generally, the fecal management member is a sheet of loop material having a backing preferably comprising a thermoplastic backing layer (e.g., of polypropylene) having front and rear major surfaces and a multiplicity of longitudinally oriented fibers in a specially formed sheet of fibers having generally non-deformed anchor portions bonded by being embedded in the backing layer at spaced elongate generally parallel bonding locations that are continuous in one direction along the front surface with arcuate portions of the sheet of fibers projecting from the front surface of the backing layer between the bonding locations in continuous rows also extending transversely across the sheet of loop material. The arcuate portions of the sheet of fibers have a generally uniform height from the backing layer of greater than about 0.5 millimeters and preferably greater than about 1.0 millimeters, the height of the formed sheet of fibers is at least one third, and preferably one half to one and one half times the distance between the bonding locations, the individual fibers in the sheet of fibers are less than 25 denier (preferably in the range of 1 to 10 denier) in size, and the sheet of fibers without the backing has a basis weight in the range of 5 to 300 grams per square meter (and preferably in the range of 15 to 100 grams per square meter) measured along the first surface to provide sufficient open area between the fibers in the sheet of fibers along the arcuate portions (i.e., between about 10 and 90 percent open area) to afford ready penetration of fecal material into the individual fibers along the arcuate portions.

Suitable materials for use as the backing include but are not limited to thermoplastic films, porous films, apertured films, apertured formed films, unapertured formed films, nonwoven webs, breathable materials, such as breathable films, including but not limited to microporous films, apertured nonwoven webs and the like. The backing is preferably a relatively thin layer having a thickness in the range of about 0.00125 to 0.025 centimeters.

The fibers in the sheet of fibers can be disposed in various directions with respect to the parallel bonding locations and may or may not be bonded together at crossover points in the arcuate portions; can be disposed in various directions with respect to the parallel bonding locations with the majority of the fibers in the sheet of fibers (i.e., over 80 or 90 percent) extending in directions at about a right angle to the bonding locations; or all of the individual fibers in the sheet of fibers can extend in directions generally at right angles to the spaced generally parallel bonding locations.

Sheet of fibers preferably has a hydrophilicity which is less than the hydrophilicity of the backing. In a preferred embodiment, the sheet of fibers themselves have a hydrophilicity gradient wherein the arcuate portions have a hydrophilicity which is less than the hydrophilicity of the bonded locations. Even in this configuration it is preferred that the bonded locations of the sheet of fibers have a hydrophilicity which is less than the hydrophilicity of the backing.

Preferably the fecal management member is secured to the topsheet in a very minimal extent to preserve the openness of the fecal management member to allow ready penetration of fecal material. More preferably, the fecal management member is not secured to the topsheet at all preserving the openness of the fecal management member and also allowing the topsheet to separate from the fecal management member creating additional void space within the disposable absorbent article. However, it is recognized that the fecal management member should be secured within the diaper to prevent it from freely moving about. The fecal management layer is positioned between the liquid pervious topsheet and the substantially liquid impervious backsheet which is joined to the topsheet. The fecal management member comprises a backing layer and a sheet of fibers. The sheet of fibers have anchor portions in the backing layer at spaced bonding locations and have arcuate portions of the sheet projecting from the backing between bonding locations. The disposable absorbent article preferably comprises an absorbent core which is positioned between the fecal management member and the backsheet.

EXAMPLES

Figure 7:
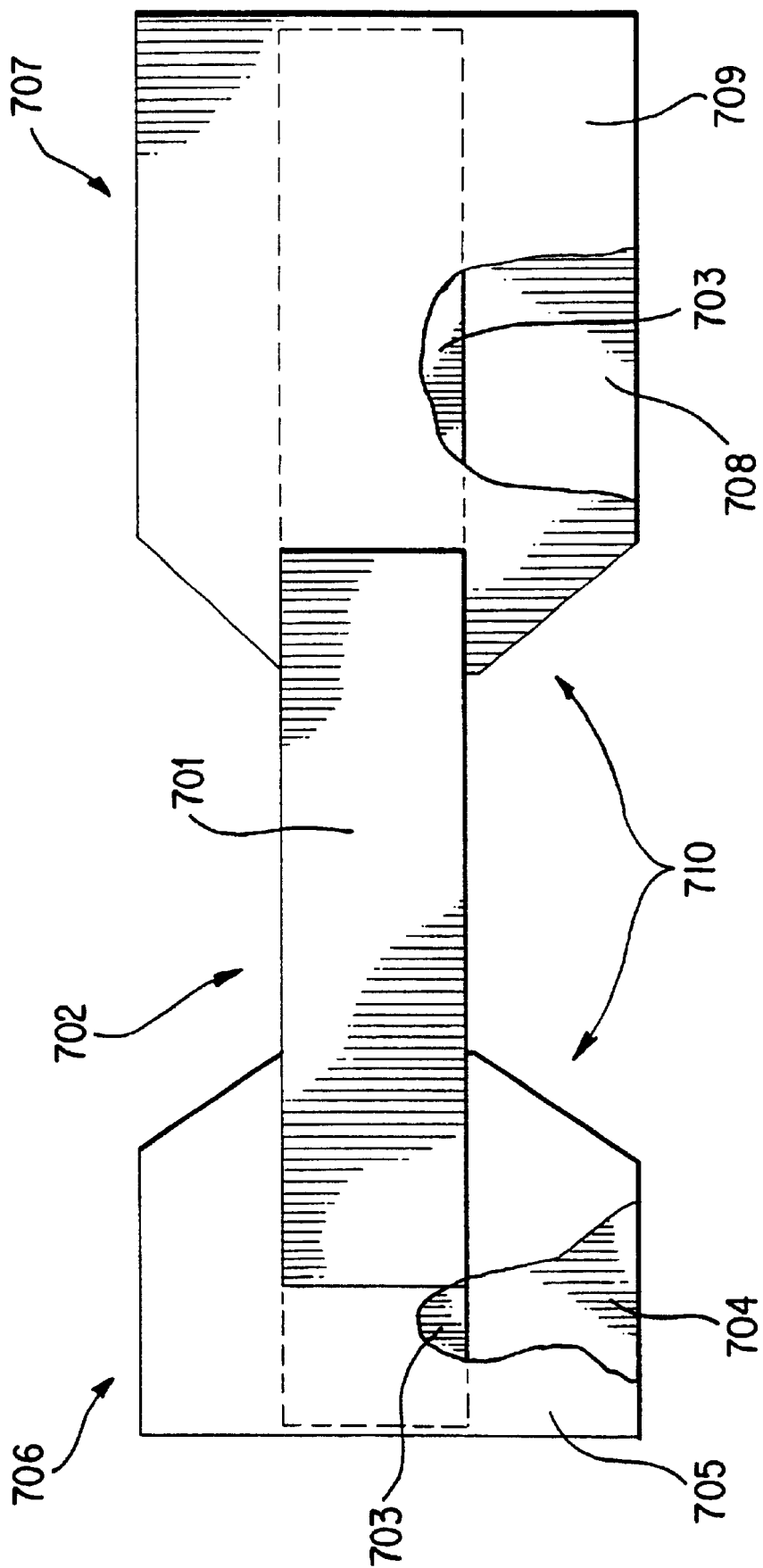
FIGS. 7 and 8 show a schematic diagram of an absorbent article according to the present invention.
Figure 8:
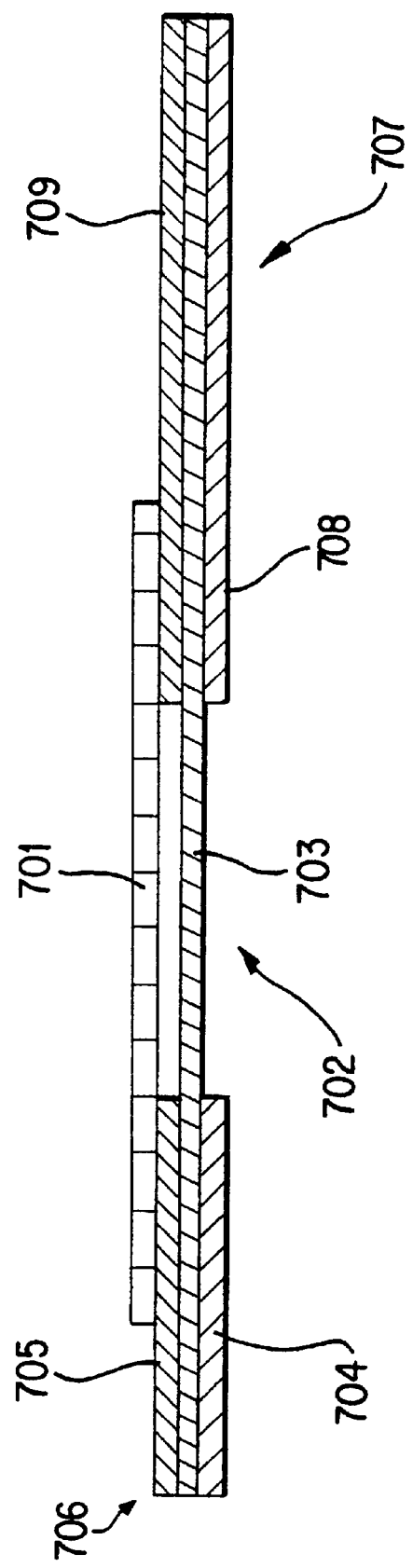

Example 1 is an absorbent article comprising an absorbent core of the present invention, schematically depicted in FIG. 7, showing a garment side view of such an absorbent core, and FIG. 8 showing a cross sectional view of such an absorbent core. The acquisition layer 701 of example 1 comprises a layer of chemically stiffened cellulosic fibers combined with a bicomponent fiber in a ratio of 87% to 13%, respectively. The acquisition layer 701 of example 1 has a longitudinal dimension of 260 mm and a transverse dimension of 60 mm. The basis weight of the acquisition layer 701 is 340 gsm resulting in a total weight of approximately 5.3 grams. The acquisition layer 701 is the layer located closest to the wearer oriented surface.

Example 1 further comprises a front storage member 704 located in the front waist region 706 and a rear storage member 708 located in the rear waist region 707. In example 1, the storage members 704 and 708 are located on the backsheet oriented surface of the absorbent core and comprise the same type of material. The storage members 704 and 708 comprise a HIPE based open celled polymeric foam designed for storage of fluid. The front storage member 704 is substantially rectangular in shape, with the exception of the shaped inner edge 710, having a width, transverse dimension, of 130 mm and a length, longitudinal dimension, of 110 mm. The basis weight of the storage member 704 is 160 gsm resulting in an approximate total weight of 2.1 grams. The rear storage member 708 is substantially rectangular in shape, excepting for the shaped inner edge 710, having a width, transverse dimension, of 130 mm and a length, longitudinal dimension, of 188 mm. The basis weight of the rear storage member 708 is 160 gsm resulting in an approximate total weight of 3.8 grams.

Example 1 further comprises a distribution member 703, which is located on the wearer oriented surface of the front and rear storage members 704 and 708, and on the backsheet oriented surface of the storage/rewet barrier members 705 and 709 . The distribution member 703 comprises a HIPE based open celled polymeric foam designed for distribution. The distribution member 703 extends from the front waist region 706 through the crotch region 702 and into the rear waist region 707. The distribution member 703 is slightly shaped having a transverse dimension of 80 mm in the front and rear waist regions 706 and 707 and a transverse dimension of 60 mm in the crotch region 702. The longitudinal dimension of the distribution member 703 is 438 mm. The basis weight of the distribution member 703 is 120 gsm resulting in an approximate total weight of 3.9 grams.

Example 1 further comprises storage/rewet barrier members 705 and 709 located on the wearer oriented surface of the distribution member 703 and the front and rear storage members 704 and 708 and on the backsheet oriented surface of the acquisition member 701. The storage/rewet barrier members 705 and 709 comprise superabsorbent material adhesively bonded to the remaining core structure. The shape of the storage/rewet barrier members approximate the shape of the storage members 704 and 708. The storage/rewet barrier members 705 and 709 have a basis weight of nominally 300 gsm. This basis weight results in a total weight of 11 grams.

Example 2 is an absorbent article comprising an absorbent core of the present invention, which is also schematically depicted in FIG. 7, showing a garment side view of such an absorbent core, and FIG. 8 showing a cross sectional view of such an absorbent core. The acquisition layer 701 of example 2 comprises a layer of chemically stiffened cellulosic fibers combined with a bicomponent fiber in a ratio of 87% to 13%, respectively. The acquisition layer 701 of example 2 has a longitudinal dimension of 260 mm and a transverse dimension of 60 mm. The basis weight of the acquisition layer 701 is 340 gsm resulting in a total weight of approximately 5.3 grams. The acquisition layer 701 is the layer located closest to the wearer oriented surface.

Example 2 further comprises a front storage member 704 located in the front waist region 706 and a rear storage member 708 located in the rear waist region 707. In example 2, the storage members 704 and 708 are located on the backsheet oriented surface of the absorbent core and comprise the same type of material. The storage members 704 and 708 comprise a HIPE based open celled polymeric foam designed for storage of fluid. The front storage member 704 is substantially rectangular in shape, with the exception of the shaped inner edge 710 having a width, transverse dimension, of 130 mm and a length, longitudinal dimension, of 110 mm. The basis weight of the storage member 704 is 160 gsm resulting in an approximate total weight of 2.1 grams. The rear storage member 708 is substantially rectangular in shape, excepting for the shaped inner edge 710 having a width, transverse dimension, of 130 mm and a length, longitudinal dimension, of 188 mm. The basis weight of the rear storage member 708 is 160 gsm resulting in an approximate total weight of 3.8 grams.

Example 2 further comprises a distribution member 703 which is located on the wearer oriented surface of the front and rear storage members 704 and 708 and on the backsheet oriented surface of the storage/rewet barrier members 705 and 709 . The distribution member 703 comprises a fibrous structure comprising chemically stiffened, twisted, and curled bulking fibers, high surface area fibers, and chemical binder additive. The distribution member 703 extends from the front waist region 706 through the crotch region 702 and into the rear waist region 707. The distribution member 703 is slightly shaped having a transverse dimension of 80 mm in the front and rear waist regions 706 and 707 and a transverse dimension of 60 mm in the crotch region 702. The longitudinal dimension of the distribution member 703 is 438 mm. The basis weight of the distribution member 703 is 120 gsm resulting in an approximate total weight of 3.9 grams.

Example 2 further comprises storage/rewet barrier members 705 and 709 located on the wearer oriented surface of the distribution member 703 and the front and rear storage members 704 and 708 and on the backsheet oriented surface of the acquisition member 701. The storage/rewet barrier members 705 and 709 comprise superabsorbent material adhesively bonded to the remaining core structure. The shape of the storage/rewet barrier members approximate the shape of the storage members 704 and 708. The storage/rewet barrier members 705 and 709 have a basis weight of nominally 300 gsm. This basis weight results in a total weight of 11 grams.

Examples 1 and 2 described above were subjected to the Whole Diaper Vertical Wicking Test as described below. The following table, Table 1, shows the grams fluid pre gram absorbent values for examples 1 and 2. Table 2 below shows the dry crotch caliper, the AWCC and the SCC for examples 1 and 2.

The following description is adopted for absorbent articles of the baby diaper type, and in particular for diapers of the MAXI size (i.e. intended for babies in a weight range of about 9 to 18 kg) but the skilled person will be able to readily adopt it for other purposes, such as for other sizes, or adult incontinence applications. The test specimen is held in a curved plexiglas device which utilizes a flexible, soft air bag which is used to simulate various baby pressures between 0.69 kPa–6.9 kPa (0.1–1 psi), and the article is loaded with subsequent gushes of liquid, with appropriate waiting time in between. The key result from this test is the time for the fluid of each of the gushes to penetrate into the article. After the loading of the article by this test, the article can be used for further analysis, such as measuring the rewet, preferably by the Post Curved Acquisition Collagen Rewet Method (PCACORM) as described hereinafter, or measuring the caliper, or measuring the liquid distribution, such as by determining the load in various sections of the article.

|  | Front | | | Crotch | | | Rear | | |
| --- | --- | --- | --- | --- | --- | --- | --- | --- | --- |
| Height | 18 cms | 13.5 cms | 9 cms | 4.5 cms | 0 cms | −4.5 cms | −9 cms | −13.5 cms | −18 cms |
| Ex. 1 | 9.6 | 9.8 | 11.8 | 18.3 | 15.1 | 12.7 | 17.0 | 14.3 | 11.6 |
| Ex. 2 | 4.9 | 6.8 | 7.6 | 9.2 | 8.8 | 10.7 | 11.8 | 10.4 | 6.9 |

TEST METHODS

General

Synthetic Urine Formulation

Unless otherwise noted, the composition of Jayco syn-urine in one liter of distilled water is:

| Potassium chloride | KCl | 2.0 g/l |
| --- | --- | --- |
| Sodiumsulfat | $Na_2SO_4$ | 2.0 g/l |
| Amonium-di-hydrogenphosphat | $(NH_4)H_2PO_4$ | 0.85 g/l |
| Di-Amoniumhydrogenphosphat | $(NH_4)2HPO_4$ | 0.15 g/l |
| Calciumchlorid 2 Hydrat | $CaCl_2$—$2H_2O$ | 0.25 g/l |
| Magnesiumchlorid Hexahydrat | $MgCl_2$—$6H_2O$ | 0.5 g/l |
| Distilled (de-ionized) water | | |

Unless otherwise noted, that testing conditions are standard laboratory conditions with 22° C. +/−2° C. and 50% +/−5% relative humidity.

CURVED ACQUISITION METHOD

The curved acquisition test methods aims at simulating the introduction of urine into a diaper. The following describes key principles of the test:

1. The diaper is held in a curved configuration to more realistically simulate the position of the diaper on a standing or sitting baby.
2. The realistic, vertical orientation requires that the liquid applied must be distributed against gravity.
3. The overall configuration provides key data on acquisition, distribution and storage of the liquid within the various materials thereby providing a better understanding of material properties, and their combined performance.
4. The apparatus includes a pressurized air cushion, allowing to better analyze products which have either a varying thickness thought various parts thereof, or which exhibit a pronounced thickness change throughout the loading process.

For the above mentioned Maxi sized diapers, the standard protocol loads the article four times with 75 ml +/−2 mls, at a rate of 15 ml/sec, delivered at one hour intervals. The present description refers to an automated procedure, including automatic data capturing. Of course, analogous systems can be used, such as manual recording of data, as long as the described principles are followed.

Figure 6:
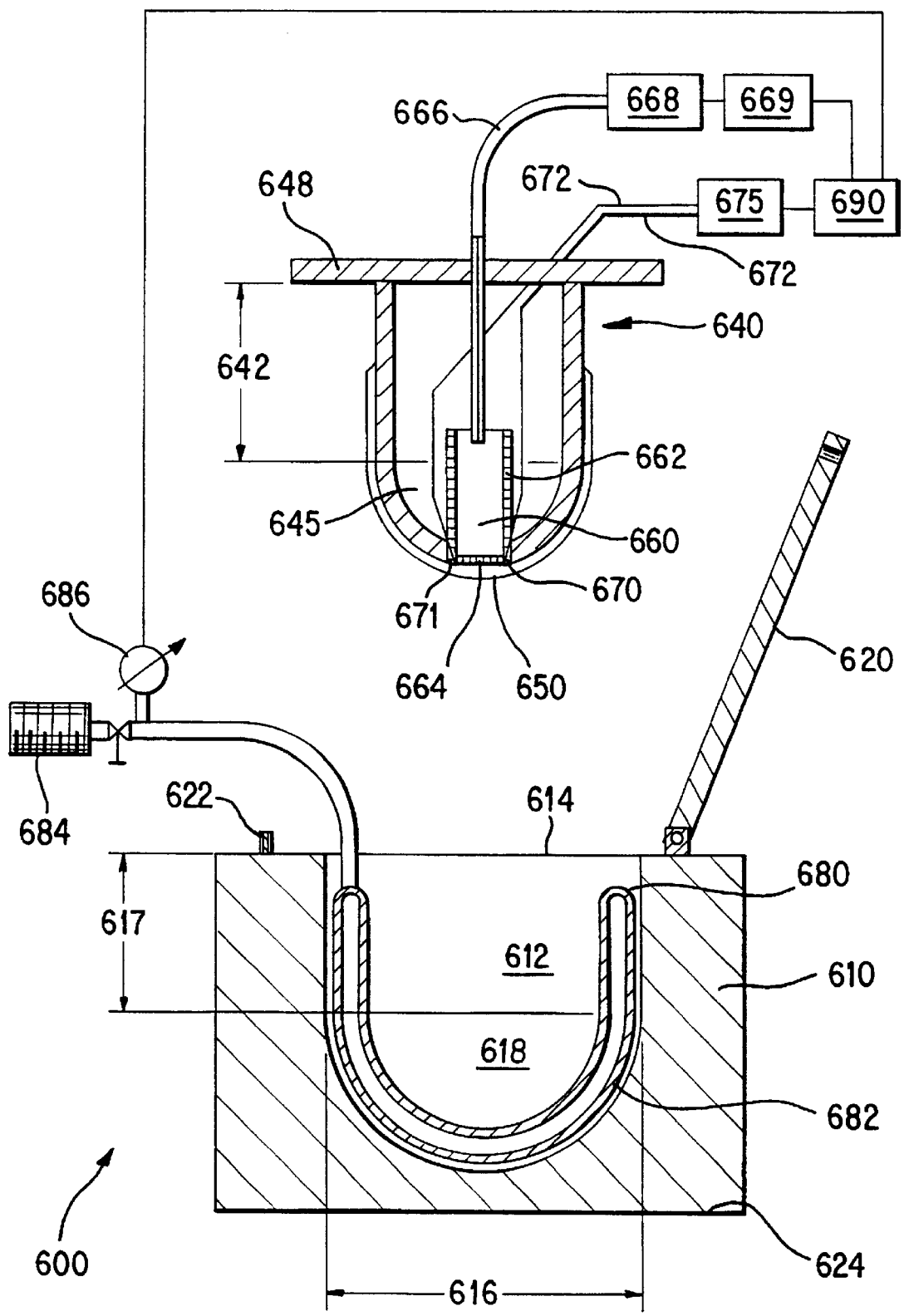
FIG. 6 is a schematic view of the apparatus used to load articles for characterization according to other procedures discussed in the Test Method section.

The test equipment is schematically depicted in FIG. 6. The complete equipment, or preferably a multiplicity thereof for ease of replication, is placed inside a controlled condition chamber, with room temperature and humidity within the following limits:

| Temperature: | 32° C. ± 2° (90° F. ± 3° F.) |
| --- | --- |
| Relative Humidity: | 50% ± 10% |

If a deviation form this protocol is deemed appropriate, this must be stated explicitly in the protocol.

The Curved Acquisition Tester (600) comprises four important parts:

a) A holding unit (610) which is essentially made of perspex/plexiglas. It has been found that suitable plates of 5 mm thickness provide sufficient strength for operating without undue deformation.

The essential part of the holding unit is a trough (612) having an upper rectangular opening (614) of 130 mm extending outside of the plane of drawing, and a width (616) of 260 mm. The rectangular through has a length (617) of about 200 mm and ends in a semicylindrical form (618) having a radius of 130 mm. The holding unit has one or more means to retain the loading unit (640) in place, here shown by a hinged lid (620) and corresponding fixation means, such as screws (622). The holding unit further comprises means for stable support (624).

b) A loading unit (640) comprising a liquid application means (660) is designed to fit into the through (612) of the holding unit (610), by having a rectangular section having a length (642) of about 180 mmm, and having cross-section of about 100 mm by 128 mm, ending in a semicylindrical section (645) having a radius of 100 mm. The loading unit further comprises a flange (648), which allows to hang the unit into the trough by being larger than said trough opening (614), and which also prevents the loading unit to be pushed out of the trough by being hold by said lid (620). The clearance for the vertical movement of the loading unit (640) is about 4 cm. The total loading unit is made from the same material as the holding unit, and can have a weight of about 1 kg, including the liquid application means.

c) The liquid application means (660) comprises a plexiglas tube (662) having an inner diameter of 47 mm, and a height of about 100 mm. It is firmly affixed to a circular opening (650) having a diameter of about 50 mm through the loading unit, positioned centered around the lowermost point of the semicylindrical portion (645). The opening of the tube is covered by a open mesh (664) (such as of wire mesh with openings of about 2 mm separated by threads of 1 mm), so as to be flush with the opening (650) of the laoding unit (640). A 6 mm diameter flexible tube (666), such as Norpren A60G (6404-17), available from Cole Parmer Instrument Company, IL, US, is connected to a test fluid metering pump (668), such as Digital Pump, Catalog, by No. G-07523-20, having a Easy-Load Pump Head, No. G-07518-02, both by Cole-Parmer Instrument Company, II, US, with a pump control unit (669) to allow start and stop of the pump based upon electrical signals. Two electrodes (670, 671) are positioned at two opposite points just inside the mesh at the lower end of the the plexiglas tubing (662), to be able to detect interruption of the electric current through the electrolyte fluid, once the tube is being emptied. The electrodes are connected via cable (672) to a time signal measuring unit (675).

d) A pressure generating means (680) comprises a flat, flexible air cushion (682), such as generally available for medical purposes (blood pressure measurement), having an uninflated dimension of 130 mm by 600 mm, which can be inflated by means of a hand pump (684) and a valve with a pressure recording device (686), which can be connecting to an electrical transducer so as to provide an electrically recordable signal corresponding to the pressure. This system is designed to operate at pressures of up to 6.89 kPa (1 psi), and is set for the standard procedure to 2.07 kPa (0.3 psi).

e) Optionally, the apparatus can comprise an automatic control unit (690), such as a suitable computer control unit, connected to the pump control unit (669), the timer (675) and the pressure recorder (686), which also can operate several measuring units in parallel. Suitable software is for example LabView® by National Instruments, Munich, Germany. A complete test equipment can be delivered by High Tech Company, Ratingen/Germany, D-64293 Darmstadt.

Steps for Setting up the Acquisition Equipment
1) Calibration of pump: before starting the experiment, the pump should be calibrated to ensure a flow rate of 75 ml per 5 seconds. If necessary, tubing should be replaced.
2) Preparation and thermal equilibration of test fluid;
3) Positioning of the cushion (682) into the trough without folds or creases;
4) Weighing of the entire article to be tested to the nearest 0.01g on a top loading balance. Marking of the urination point (1.9 forward positioned from the crotch point by 1.25 in (3.2 cm) for Girl MAXI sized diapers, 2.5 in (6.4 cm) for Boy MAXI sized diapers, and 1.875 in (4.8 cm) for Unisex MAXI diapers) onto the article with a pen.

Positioning and fixation (such as by suitable adhesive tape) of the test specimen to the loading unit, such that the liquid receiving surface is oriented towards the loading unit (and hence the backsheet towards the cushion), so as to have the opening aligned with the loading point of the article. The article is then positioned onto the curved loading unit without cutting the leg elastics or other elastic, if present, with the marked urination point located under the center of the tube (660), and attached to the loading unit by suitable attachment means, such as tape. The article is then positioned together with the loading unit into the tester, and the electrode cables are connected.

5) The lid (620) is closed, and fixed with screws (622).
6) The cushion (682) is then inflated to the desired pressure, i.e. 2.07 kPa (0.3 psi), thereby pushing the loading unit against the lid, and thus exerting the pressure on the testing article.
7) The end of the flexible tube (666) is positioned such that it directs to the center of the opening (650), and extends about 5 cm (2 in) into the tube (662).
8) The liquid pump (668) is started for the preset time (i.e. 5 seconds), and at the same time acquisition time timer (675).
9) Upon emptying of the plexiglass tube (662) the electrodes (670, 671) provide a signal stopping the acquisition time timer, upon which the waiting time is started at the timer for 60 minutes.
10) The loading cycle (step 7 and 8) is repeated to a total of four times.

Results

Upon finishing of the above cycle, the respective acisition rates can be calculated for each "gush" by dividing the load per gush (i.e. 75 ml) by the time in seconds required for each gush. (If the acquisition rates are getting close to the liquid delivery rates (i.e. 15 ml/sec), test conditions can be changed and respectively recorded.)

POST CURVED ACQUISITION COLLAGEN REWET METHOD

Before executing the test, the collagen film as purchased from NATURIN GmbH, Weinhein, Germany, under the designation of COFFI (or equivalent) and at a basis weight of about 28 g/m$^2$ is prepared by being cut into sheets of 90 mm diameter e.g. by using a sample cutter device, and by equilibrating the film in the controlled environment of the test room, 21 C +/−2 C and 50% Rh +/−10% Rh for at least 12 hours (tweezers are to be used for all handling of the collagen film).

At least 55 minutes, but not more than 65 minutes after the last gush of the Curved Acquisition Test is absorbed, the article is removed from the curved acquisition apparatus and the article is carefully placed flat on a lab bench.

4 sheets of the precut and equilibrated collagen material are weighed with at least one milligram accuracy, and then positioned centered onto the loading point of the article, and covered by perspex plate of 90 mm diameter, and about 20 mm thickness. A weight of 15 kg is carefully applied (also centred). After 30+/−2 seconds the weight and perspex plate are carefully removed and the collagen films are reweighed.

The Post Curved Acquisition Collagen Rewet Method result is the moisture pick up of the collagen film, expressed in mg.

It should be noted further, that this testing protocol can be adjusted easily according to specific product types, such as different baby diaper sizes, or adult incontinence articles, or catamenial articles, or by the variation in the type and amount of loading fluid, the amount and size of the absorbent material, or by variations in the applicable pressure. Having once defined these relevant parameters, such modifications will be obvious to one skilled in the art. When considering the results from the adjusted test protocol the products can easily be optimized for the identified relevant parameter such as in a designed experiment according to standard statistical methods with realistic in use boundary conditions.

The rewet method disclosed above is designed for an article with a 90 mm or wider width crotch whereon the 90 mm diameter test apparatus can be applied. For absorbent cores with narrower crotch widths a reduction in diameter of the test apparatus to match the crotch width is required. Additionally, a reduction in the applied weight is also required to maintain an equal pressure per unit area between the different measurements. The rewet values for different crotch widths can be normalized for crotch width by multiplying with the square of the ratio of 90 mm to the actual diameter (in mm)

CALIPER MEASUREMENT METHOD

The intent of this method is to provide a procedure to determine the thickness of the absorbent article at the crotch point and in either of the waist regions immediately adjacent the crotch region. The test can be executed with a conventional caliper gauge, such as Type EG-225 available from ONO SOKKI Technology Inc. IllI. US, with an appropriate gauge stand, having an aluminium circular sample foot of 41mm diameter, having a weight of foot of 10 g. An additional weight is added to achieve a total of 160 g to adjust the pressure to 1.18 kPa (0.173 psi).

Measurement Points

The key measurement points are the crotch point and the waist points in the waist regions immediately adjacent the crotch region. The crotch point, and crotch region should be determined as described previously for a given design. The crotch point and a laterally oriented lines delimiting the crotch region and waist regions of the core should be marked on the article. Once defined, the measurement at the crotch point entails placing the sample contact foot centered over the crotch point. For measurements in either of the waist points, the sample contact foot should be placed in one of the waist regions in the center of the pad, laterally, with the outer edge of the sample contact foot contacting the crotch region delimiting line. This is considered to be the waist point immediately adjacent of the crotch region.

Basic Protocol

1. The absorbent article is positioned under the caliper gauge with the wearer surface toward the sample contact foot.
2. The sample contact foot is gently lowered into contact with the surface of the article.
3. The caliper reading is taken 5 seconds after the foot comes into contact with the article.

Saturated Crotch Caliper (SCC)

1. The elastics of the article to be measured must be cut to allow the article to lay flat.
2. The article is then placed in its flat state into a large container, containing and excess of synthetic urine solution, see Curved Acquisition Test method. The amount of fluid in the container should be 4 to 5 times to total absorbent capacity of the , i.e. 2.07 kPa (0.3 psi).
3. The article is submerged and allowed to absorb the liquid for 15 minutes.
4. After 15 minutes the article is removed and the caliper is measured, described above, at the crotch point and the measurement recorded.

Actual Wet Crotch Caliper (AWCC) and Actual Wet Waist Caliper

1. The article is loaded as described in the Curved Acquisition Protocol.
1. After the final 1 hour waiting period the article is removed and the elastics cut to allow it to lay flat.
2. The article caliper is then measured, described above, at the crotch point and in both waist regions immediately adjacent the crotch region and the measurements are recorded.

Absorbent Core Capacity and Absorbent Core Crotch Capacity by Teabag Centrifuge Capacity Test (TCC Test)

Whist the TCC test has been developed specifically for superabsorbent materials, it can readily be applied to other absorbent materials, it can readily be applied to the other absorbent materials.

The Teabag Centrifuge Capacity test measures the Teabag Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two liters of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing devuce (e.g. VACUPACK2 PLUS from Krups, Germany).

The teabag is opened by carefully cutting it partially, and is then weighed. About 0.200 g of the sample of the absorbent material, accurately weighed to +/−0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately.

After 20 minutes soaking time the sample teabag and the blank teabag are removed from the saline solution, and placed in a Bauknecht WS130, Bosch 772 NZK)096 or equivalent centrifuge (230 mm diameter), so that each bag sticks to the outer the speed increased quickly to 1,400 rpm. Once the centrifuge has been stabilized at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

TCC=[(sample teabag weight after centrifuging)−(blank teabag weight after centrifuging)−(dry absorbent material weight)] ÷(dry absorbent material weight).

Also, specific parts of the structures or the total absorbent articles can be measured, such as "sectional" cut outs, i.e. looking at parts of the structure or the total article, whereby the cutting is done across the full width of the article at determined points of the longitudinal axis of the article. In particular, the definition of the "crotch region" as described above allows to determine the "crotch region capacity". Other cut-outs can be used to determine a "basis capacity" (i.e. the amount of capacity contained in a unit area of the specific region of the article. Depending on the size of the unit area (preferably 2 cm by 2 that defines how much averaging is taking place—naturally; the smaller the size, the less averaging will occur.

Capillary Sorption Test

The purpose of this test to measure the capillary sorpion absobent capacity, as a function of height, of storage absorbent members of the present invention. (The test is also used to measure the capillary sorption absorbent capacity, as a function of height, of the materials - i.e., without osmotic absorbent, such as hydrogel-forming absorbent polymer, or other optional materials utilized in Capillary Sorption method as it pertains to measuring an entire storage absorbent member.) Capillary sorption is a fundamental property of any absorbent that governs how liquid is absorbed into the absorbent structure. In the Capillary Sorption experiment, capillary sorption absorbent capacity is measured as a function of fluid pressure due to the height of the sample relative to the test fluid reservoir.

The method for determining capillary sorption is well recognized. See Burgeni, A. A. and Kapur, C., "Capillary Sorption Equilibria in Fiber Masses," Textile Research Journal, 37 (1967), 356–366; Chatterjee, P. K., Absorbency, Textile Science and Technology 7, Chapter II, pp 29–84, Elsevier Science Publishers B. V, 1985; and U.S. Pat. No. 4,610,678, issued Sep. 9, 1986 to Weisman et al. for a discussion of the method for measuring capillary sorption of absorbent structures. The disclosure of each of these references is incorporated by reference herein.

A porous glass frit is connected via an uninterrupted column of fluid to a fluid reservoir on a balance. The sample is maintained under a constant confining weight during the experiment. As the porous structure absorbs/releases fluid upon demand, the weight loss/gain in the balance fluid reservoir is recorded as fluid uptake, adjusted for uptake of the glass frit as a function of height and evaporation. The uptake or capacity at various capillary suctions (hydrostatic tension or heihts) is measured. Incremental absorption/Desorption occurs due to the incremental lowering/raising of the frit (i.e., decreasing/increasing capillary suction).

Time is also monitored during the experiment to enable calculation of initial effective uptake rate (g/g/h) at a given height.

The test liquid used in this test is the synthetic urine as described in the above., and a deatailed description can be found in PCT application 09/674,225 U.S. Pat. No. 6,664,439 (P&G docket number (CM 1755MQ), which is incorporated herein by reference. The key resul are:

The Capillary Sorption Desorption Height at which the material has released x% of its capacity achieved at 0 cm (i.e. of CSAC 0), (CSDH x) expressed in cm; The Capillary Sorption Desorption Height at which the material has released 50% of its capacity (CSDH 50) is also referred to as Medium Desorption Pressure (MDP), expressed in cm (of water column).

The Capillary Sorption Absorption Height at which the material has absorbed y % of its capacity achieved at 0 cm (i.e. of CSAC 0), (CSAH y) expressed in cm;

The Capillary Sorption Absorbent Capacity at a certain height z (CSAC z) expressed in units of g {of fluid}/g {of material}; especially at the height zero (CSAC 0), and at heights of 35 cm, 40 cm, etc.

The Capillary Sorption Absorption Efficiency at a certain height z (CSAE z) expressed in %, which is the ratio of the values for CSAC 0 and CSAC z.

In use Article Total Absorbent Capacity and Article Crotch Region % Capacity

The following protocol is intended to provide the Total Absorbent Capacity ("TAC") as well as, the Crotch Region Capacity ("CRC") of the article. The protocol uses data obtained from in-use testing of articles by panelists.

Panelist Selection

Panelists should be recruited by weight, within the intended size range of the articles being tested. Currently, the product sizes and baby weights for marketed Pampers, Luvs® as sold by The Procter & Gamble Co. in Europe and Huggies® as sold by Kimberly-ClarcInc. in Europe are as follows(as of Mar. 25, 1997):

| Diaper Size | Newborn | Small | Small/Medium | Medium | Large | X-Large |
| --- | --- | --- | --- | --- | --- | --- |
| Pampers ® | up to 10 lbs | 8–14 lbs | 12–18 lbs | 16–28 lbs | over 22 lbs | over 27 lbs |
| Luvs ® | na | 8–15 lbs | 12–18 lbs | 16–28 lbs | 21–37 lbs | over 30 lbs |
| Huggies ® | up to 10 lbs | 8–14 lbs | 12–18 lbs | 16–28 lbs | 22–37 lbs | over 30 lbs |

A group of 100 panelists should be recruited uniformly across the appropriate weight range relative to the size of article being tested and the entended user group. Note: the above sizes are for currently marketed articles and should be adopted as article designs and or sizes are modified.

Following the recruiting step, 30 panelists are to be selected from the group at random.

Article Set-up

The test articles are weighed to provide a dry article weight.

The panelist removes the article the child is wearing when the test begins, i.e. the panelist's own article, and the panelist applies the test article, in the panelist's normal fashion.

Once the test article is applied, the panelist places the wearer in the standing position and the crotch point is determined as previously described in this application.

The crotch point is then marked on the outside of the test article in a permanent fashion, as well as the corresponding crotch region as derived from the core dimensions.

The loading point is then determined by measuring from the crotch point forward to the appropriate genital point relative to the sex and size of the wearer. The distance forward from the crotch point for females in the medium size is 1.25 inches (3.2 cm); the distance forward from the crotch point for males in the medium size range is 25 inches (6.4 cm).

It is apparent to one skilled in the art that these distances may increase or decrease with the size of the wearer.

Therefore, for the other sizes, the distance can be determined by placing the wearer in a standing position and determining the crotch point as specified previously, and then measuring from the crotch point to the urethra or base of the penis.

Once the loading point is determined, the distance from the front waist to the loading point is measured; this distance is used to establish the length of the loading tube to be inserted into the article during the syn-urine loading.

Synthetic Urine

The test fluid to be used for the test is synthetic urine (syn-urine) as described in the above.

The temperature in the syn-urine bath is to be held at 37° C. A suitable heated bath is Lauda M20-B available from VWR Scientific Producers.

Delivery pumps are to be used to pump the syn-urine from the heated bath to the article. The volume and rate of the delivery is to be 75 ml at 15 ml/sec. Suitable pumps include Masterflex Models 7550-60 or 7524-00 available from Cole Parmer Instrument Company. The inner diameter of the loading tube is to be 0.125 in (0.3175 cm).

Protocol

Once the articles are applied and marked as described above, loose fitting blue cotton pants are weighed to provide a dry pants weigth and then the pants are applied over the test article so that leakage can be easily identified and measured.

The test articles are then loaded by inserting the loading tube to the predetermined distance, as measured from the waist, and applying the specified loading at the specified rate.

Between loads, the wearer returns to normal activity.

The articles are loaded with the specified load and rate every 10 minutes, i.e. 10 minute intervals between loads.

These loadings are continued until about 1 gram of fluid leaks from the article onto the cotton. Thi can be determined by removing the pants and weighing them.

Once at least 1 gram of fluid has leaked onto the pants, the test article is removed and is immediately weighed.

Total Capacity and Crotch Region Capacity

The total capacity for a given test article can also be determined by subtracting the dry article weight of the given article from the wet article weihgt of that seme article.

The total capacity for the group is the average of the total capacities of the individual articles.

Crotch region capacity is determined by laying the loaded article flat and cutting the crotch region out of the article. This region is the weighed. This procedure should be conducted within 15 minutes of removal of the a rticle from the wearer.

A corresponding crotch region is cut from a dry article to provide a dry crotch region weight.

The crotch capacity is determined by subtracting the dry crotch region weight from the wet crotch region weight. This provides the crotch capacity for a given article.

The crotch capacity for the group of articles is considered to be the average of the individual crotch region capacities.

The crotch region capacity as a percent of the total is determined by dividing the average crotch region capacity by the average total capacity for a given set of articles.

A similar procedure is used to determine the percent absorbent capacity of the absorbent core behind the crotch point.

C. CROTCH WIDTH WHEN WET

The crotch width of an absorbent core of an absorbent article is measured by first determining the crotch point of the absorbent article. The article is then wetted to 70% of it's total capacity in accordance with the Fluid Acquisition method. The article is removed from the apparatus and is allowed to equilibrate for 1 hour. Upon equilibration, the article is cut transversely through its thickness to provide a 2 in (5 cm) long section, where the crotch point is at the transverse and longitudinal center of the section. Each of the wetted layers of the sectioned sample are then weighed. The width of the narrowest layer at the crotch point corresponds to the crotch width of the absorbent core.

WHOLE ARTICLE VERTICAL WICKING TEST

The articles are weighed prior to testing. The preweighed articles are mounted on a lucite plate (6 in by 14 in and ⅜ in thick, respectively 15.2 cm by 35.5 cm and about 0.95 cm thick) with the substantially liquid impervious backsheet adjacent the plate surface. The article is wrapped around the edge of the plate with the longitudinal dimension of the article parallel to the long dimension of the plate. When the article tested is asymmetric the crotch point is located at the edge of the plate. The waist line edges of the article are mounted on the plate with tape, the elastication elements being cut in 2 or 3 places to facilitate the mounting.

The plate is suspended vertically over a fluid bath contained in a glass tray with the longitudinal dimension of the article perpendicular to the fluid surface. The test is conducted at 32° C. to more accurately simulate in use conditions. The fluid is then brought into contact with the lower edge of the article so that the article edge remains immersed (i.e. the assembly of lucite plate and article is immersed such that the liquid is in level with the lower edge of the plate), and is maintained in this position for 15 minutes. The article is then removed from fluid contact and allowed to hang in the same vertical orientation for 15 minutes equilibration. After equilibration the articles are removed from the plate and weighed and the fluid pick up is noted.

After weighing, the articles are laid horizontally flat on a 3 in by 15 in (76 mm by 381 mm) cutting pattern which was segmented 1.7 in (43.2 mm) wide zones, i.e. for a Maxi sized diaper as an article, 9 such zones would result. The article is then cut through the central portion into segments measuring 1.7 inches by 3 inches. The absorbent component in each segment is weighed, oven dried and reweighed and the fluid pick-up determined in a gram per gram basis (corrected for deposited solids from the fluid).

The synthetic urine composition comprised 0.31 g $CaH_4(PO_4)_2$ $H_2O$, 0.68 g $KH_2PO_4$, 0.48 g $MgSO_4$ $7H_2O$, 1.33 g $K_2SO_4$, 1.24 g $Na_3PO_4$ $12H_2O$, 4.4 g NaCl, 3.16 g KCl, 8.56 g Urea. Distilled water is used as the solvent. The components were added to 900 mls of distilled water in the order given and each dissolve before the next component was added, and finally diluted to 1 liter.

Distribution Materials Vertical Wicking Test

The vertical wicking test is aiming at evaluating the time required for a fluid front to reach a certain height in a vertical arrangement, i.e. against gravity, as well as amount of fluid picked up by the material during this time.

The principle of this test is to place a sample onto a sample holder equipped with electrodes in form of pins, both functioning to fix the sample in a vertical position and to allow generation of an electrical timer signal. The reservoir of the fluid is positioned on a scale, such that the time dependency of the fluid pick up in the sample resulting from the vertical wicking can be monitored. The test is described in detail in PCT application US 97/05234 (P&G docket number CM1454) as Vertical Wicking Test. Whilst not being essential to the test, the test can be executed based on a commercially available equipment, the EKOTESTER of Ekotec Industrietechnik GmbH, Ratingen, Germany, which also allowed electronic processing of the data.

What is claimed is:

1. An absorbent article for acquiring and containing fluid, the absorbent article comprising:

a topsheet;

a backsheet joined to said topsheet; and an absorbent core for acquiring and storing fluid deposited on the absorbent article, said absorbent core being positioned between said topsheet and said backsheet, said absorbent core comprising:

a) an acquisition region for acquiring fluid, said acquisition region comprising an acquisition material having acquisition material having
      i) a medium desorption presure (MDP) value of at least about 5 cm but less than about 18 cm; and
      ii) an initial acquisition rate of at least about 5 ml/sec measured in a Curved Acquisition Test; and
   b) a distribution region for distributing fluid away from the area of initial deposit, said distribution region being in fluid communication with said acquisition region, said distribution region comprising a distribution material having
      i) a capillary absorption pressure of at least about 24 cm;
      ii) a vertical wicking rate to a height of 5 cm in no more than about 15 minutes; and
      iii) a vertical wicking absorbent capacity of at least about 5 g/g at a height of about 20 cm.

2. The absorbent article of claim 1 wherein said absorbent core additionally comprises a storage region in fluid communication with said distribution region, said storage region comprising a storage material, at least a portion of said storage material being positioned between said distribution material and said backsheet.

3. The absorbent article of claim 2 wherein said storage region comprises two separated storage subregion offset from each other.

4. The absorbent article of claim 2 additionally comprising rewet means for preventing rewet of liquid from said absorbent core through said topsheet, said rewet means positioned between at least a portion of said absorbent core and said topsheet.

5. The absorbent article of claim 1 wherein said distribution material comprises a fibrous or foam material.

6. The absorbent article of claim 5 wherein said distribution material comprises a HIPE foam.

7. An absorbent article for acquiring and containing fluid, the absorbent article comprising:

a topsheet;

a backsheet joined to said topsheet; and an absorbent core for acquiring and storing fluid deposited on the absorbent article, said absorbent core being positioned between said topsheet and said backsheet, said absorbent core comprising:

a) an acquisition region for acquiring fluid, said acquisition region comprising an acquisition material having
      i) a medium desorption pressure (MDP) value at least about 5 cm but less than about 15 cm; and
      ii) an initial acquisition rate of at least about 10 ml/sec measured in a Curved Acquisition Test; and
   b) a distribution region for distributing fluid away from an area of initial deposit, said distribution region being in fluid communication with said acquisition region, said distribution region comprising a distribution material having
      i) a capillary absorption pressure of at least about 30 cm;
      ii) a vertical wicking rate to a height of 5 cm in no more than about 5 minutes; and
      iii) a vertical wicking absorbent capacity of at least about 20 g/g at a height of about 20 cm; and
   c) a storage region for storing fluid, said storage region being in fluid communication with at least a portion of said distribution region, said storage region comprising a storage material.

8. The absorbent article of claim 7 wherein said acquisition material has a fourth gush acquisition rate of at least about 0.50 ml/sec in the Curved Acquisition Test.

9. The absorbent article of claim 8 wherein said distribution material has a time to Wick to 12.4 cm of less than about 100 sec when measured according to the Distribution Material Vertical Wicking test.

10. The absorbent article of claim 9 wherein said distribution material has a Capillary sorption desorption height at 90% of desorbed capacity of at least 40 cm.

11. The absorbent article of claim 10 wherein said storage material satisfies at least one of the following requirements when submitted to the Capillary Sorption test: (a) a Capillary Sorption Absorption Capacity at 35 cm (CSAC 35) of at least 15 g/g; and/or (b) a Capillary Sorption Absorption Capacity at 0 cm (CSAC 0) of at least 15 g/g and a Capillary Sorption Absorption Efficiency at 40 cm (CSAE 40) of at least 55%; and/or (c) a Capillary Sorption Absorption Height at 50% of its capacity at 0 cm absorption height (CSAH 50) of at least 35 cm.

12. The absorbent article of claim 11 additionally comprising rewet means for preventing rewet of liquid from said absorbent core through said topsheet, said rewet means positioned between at least a portion of said absorbent core and said topsheet.

13. A The absorbent article of claim 12 wherein said distribution material comprises a HIPE foam.

14. The absorbent article of claim 13 wherein said storage material is selected from the group consisting of:
   (a) a polymeric foam material;
   (b) high surface area fibers;
   (c) hydrogel forming materials; or
   (d) combinations thereof.

15. A disposable absorbent article for acquiring and containing fluid, the absorbent article comprising:

a topsheet;

a backsheet joined to said topsheet; and an absorbent core for acquiring and storing fluid deposited on the absorbent article, said absorbent core being positioned between said topsheet and said backsheet, said absorbent core having a crotch region and a pair of waist regions joined to said crotch region, said absorbent core comprising:

a) an acquisition region for acquiring fluid, said acquisition region comprising an acquisition material having
      i) a Medium desorption pressure (MDP) value at least about 5 cm but less than about 15 cm, and ii) an Initial Acquisition Rate of at least about 10 ml/sec measured in a Curved Acquisition Test; and b) a distribution region for distributing fluid away from an area of initial deposit, said distribution region being in fluid communication with said acquisition region, said distribution region comprising a distribution material having i) a capillary absorption pressure of at least about 40 cm;

ii) a vertical wicking rate to a height of 5 cm in no more than about 5 minutes; and iii) a vertical wicking absorbent capacity of at least about 40 g/g at a height of about 20 cm; and c) a storage region for storing fluid, said storage region being in fluid communication with at least a portion of said distribution region, said storage region comprising a storage material.

16. The absorbent article of claim 15 wherein the absorbent article has a Saturated Crotch Caliper (SCC); an Actual Wet crotch Caliper (AWCC) less than about 10 mm; the AWCC being less than 50 of the SCC; and a post Curved Acquisition Collagen Rewet Value of less than 100 g.

17. The absorbent article of claim 16 wherein said absorbent core has a crotch width of less than about 70 mm.

* * * * *